(12) United States Patent
Clendennen et al.

(10) Patent No.: US 6,392,122 B1
(45) Date of Patent: May 21, 2002

(54) APPLE PROMOTERS FOR EXPRESSION OF TRANSGENES IN PLANTS

(75) Inventors: Stephanie K. Clendennen; Debra K. Schuster, both of Portland, OR (US)

(73) Assignee: Agritope, Inc., Portland, OR (US)

( * ) Notice: Subject to any disclaimer, the term of this patent is extended or adjusted under 35 U.S.C. 154(b) by 0 days.

(21) Appl. No.: 09/560,419

(22) Filed: Apr. 27, 2000

Related U.S. Application Data

(60) Provisional application No. 60/132,124, filed on Apr. 30, 1999.

(51) Int. Cl.[7] .................. C07H 12/04; C12N 15/11; C12N 15/82; C12N 15/67
(52) U.S. Cl. .................. 800/287; 536/24.1; 435/320.1; 435/419; 435/468; 800/295
(58) Field of Search ............... 435/320.1, 468, 435/410, 419; 536/23.1, 23.6, 24.1; 800/278, 287

(56) References Cited

PUBLICATIONS

Atkinson, R. G. et al., "Apple ACC–oxidase and polygalacturonase: ripening–specific gene expression and promoter analysis in transgenic tomato." 1998, Plant Molecular Biology, vol. 38, pp. 449–460.*

Meier, I. et al., "The tomato RBCS3 A promoter requires integration into the chromatin for correct organ–specific regulation." 1997, FEBS Letters, vol. 415, pp. 91–95.*

Montgomery, J. et al., "Identification of an ethylene–responsive region in the promoter of a fruit ripening gene." 1993, Proc. Natl. Acad. Sci. USA, vol. 90, pp. 5939–5943.*

Atkinson, R.G., et al., "Apple ACC–oxidase and polygalacturonase: ripening–specific gene expression and promoter analysis in transgenic tomato" *Plant Molecular Biology* 38:449–460 (1998).

Belanger, F.C., et al., "Evidence for the thiamine biosynthetic pathway in higher–plant plastids and its developmental regulation" *Plant Molecular Biology* 29:809–821 (1995).

Clendennen, S.K., and May, G.D., "Differential Gene Expression in Ripening Banana Fruit" *Plant Physiol.* 115:463–469 (1997).

Jacob–Wilk, D., et al., "Induction of a Citrus gene highly homologous to plant and yeast thi genes involved in thiamine biosynthesis during natural and ethylene–induced fruit maturation" *Plant Molecular Biology* 35:661–666 (1997).

Jefferson, R.A., et al., "GUS fusions: β–glucuronidase as a sensitive and versatile gene fusion marker in higher plants" *The EMBO Journal* 6(13):3901–3907 (1987).

Pear, J.R., et al., "Isolation and characterization of a fruit–specific cDNA and the corresponding genomic clone from tomato" *Plant Molecular Biology* 13:639–651 (1989).

Robinson, H.L., and Torres, C.A.T., "DNA vaccines" *seminars in Immunology*; 271–283 (1997).

Sung, S–K., and Gynheung, A., "Molecular cloning and characterization of MADS–box cDNA clones of the fuji apple" Proceedings of the 5th International Congress of Plant Molecular Biology, abstract 403 (1997).

Yao, J–L., et al., "Seven MADS–box Genes in Apple are Expressed in Different Parts of the Fruit" *J. Amer. Soc. Hort. Sci.* 124(1):8–13 (1999).

* cited by examiner

*Primary Examiner*—Gary Benzion
*Assistant Examiner*—David H Kruse
(74) *Attorney, Agent, or Firm*—Linda R. Judge; Perkins Coie LLP

(57) ABSTRACT

The present invention is directed to apple fruit-associated and Thi 1.3:actin fusion promoters capable of promoting the expression of heterologous genes. The invention provides apple fruit-associated and Thi 1.3:actin fusion promoters together with heterologous nucleic acid constructs, vectors, kits, transformation methods, transgenic plant cells and transgenic plants comprising such promoters.

15 Claims, 4 Drawing Sheets

```
          10          20          30          40          50
AAGCTTTAGATCTCATGGGCGATGTGGATGTCACAATCCACCCCCCTTA
          60          70          80          90         100
GGGGCCCGACGTCCTCGTCATCACACTTCCGGCCAGGGATTGGCTCTAAT
         110         120         130         140         150
ACCATTTGTCACATCCCGGCCCGGATCCACCACATCTCAAGCCCGTTCCA
         160         170         180         190         200
CCACCGTAGCATGATATTGTCCGCTTTGGGCTTACCATTCCCTCACGGTT
         210         220         230         240         250
TTGTTTTTGGGAACTCACGAGCAACTTCCTAGTGGGTCACCCATCCTGGG
         260         270         280         290         300
AGTGTTTAACTTCGGAGTTCCTACGAAACCCGAAGCCAATGAGCTCCCAA
         310         320         330         340         350
AAGGTCTCGTGCTAAGTAGGGATGAGAATATACATTTAAGGATTACTCCC
         360         370         380         390         400
CTGGGCGATGTGGGATGTCACAATTTGGGTAAGAAAATGACAAGATCAAA
         410         420         430         440         450
TTAAAACTGTCAAATTTTATGCAAATTTGAAAAACAATTACAAAATCTTA
         460         470         480         490         500
AGGAAAGTATAACATTAGTGCTTTTTTTTTGTTCCAAGAAGCATTAACA
         510         520         530         540         550
TACAATTTGTTATGATATATTAATATGCAATGATTTTAAACATTAATGCA
         560         570         580         590         600
TTTTTTTTTCATTAATCCCTCCCTTCAAATATGCATAGAATTTAATGTAT
         610         620         630         640         650
ACATTAAAACTTTAATTAGGGGTGTTTTAGGCATCTAAAAAAATGCAAAA
         660         670         680         690         700
TGTGTAAAGGCAAATAGAATTAATGACTTTGCTTATGTGGAGCCTAGTCA
         710         720         730         740         750
TTAGGTTTTATTTAGATAAAAAGACTATGTCAGGTTTTATGTAAAGAAAC
         760         770         780         790         800
TTGAGTTTCAAGAGCTAAAGTCATATTTTCAGTAGAAATTAAACACATTA
         810         820         830         840         850
ATCAACACTTGAGTAATAAAATGATCATCAACAATCTAATCATTTGGTTT
         860         870         880         890         900
ACAAATTGAGAAATACTAAGGAGACTGTTTCAAAGTAAGACTTCCTATGA
         910         920         930         940         950
ACTCTCTATCACCTCATATTCTTGGCACAAAATTTTATAACATTAACATA
         960         970         980         990        1000
AGAATTGTATCAACAACATAAAATGGCAGAAAGTTCGTAGAAAATCACAT
                              >putative_TATA_box
                              |
        1010        1020        1030        1040        1050
TCAAGATAATAGCCTTAGCAATTCCCTTATAAACTTTGTCATCTAACATT
        1060        1070        1080        1090        1100
TCCCTCTCTATTCACTCTCCTCACACTCAAACACACACCGTGGACTGGTT
        1110        1120        1130        1140        1150
CATGCTTGCCACTTGTACCTCCCAAGAGGTTCTAGACCCTTCATATCCTA
        1160        1170        1180        1190        1200
TCCTCTTCCCACGTGTCCATCTTCAATTTTACATATACGTCACCCTCCTC
        1210        1220        1230        1240        1250
CTTAAATAACCACTCTCTTCACTTCCATCTTCTGACTTGCAAACGCTAAA
        1260        1270        1280        1290        1300
CCCCCAAATCACCCCATCTTATCATCTTCTCTCTCTCTCCCTCTCTCTCC
        1310        1320
TTCTCTCGCATCAATCCATGG
```

Fig. 1

```
        10         20         30         40         50
AAGCTTTAGATCTCATGGGCGATGTGGGGATGTCACAATTTGGGTAAGAT
        60         70         80         90        100
AATGACAAGATCAAATTAAAACTGTCAAATTTTAGGCAAATTTGAAAAAC
       110        120        130        140        150
AATTACAAATCTTAAGGAAAGTATAACATTAGTGCTTTTTTTTTGTTCC
       160        170        180        190        200
AAGAAGCATTAACATACAATTTGTTATGATATATTAATATGCAGTGATTT
       210        220        230        240        250
TAAACATTAATGCATTTTTTTTTCATTAACCCCTCCCTTCAAATATGCAT
       260        270        280        290        300
AGAATTTAATGTATACATTAAAACTTTAATTAGGGTGTTTTAGGCATCT
       310        320        330        340        350
AAAAAAATGCAAAATGTGTAAAGGCAAATAGAATTAATGACTTTGCTTAT
       360        370        380        390        400
GTGGAGCGTAGTCATTAGGTTTTATTTAGATAAAAGACTATGTCGGGTT
       410        420        430        440        450
TTATGTAAAGAAACTTGAGTTTCAAGAGCTAAAGTCATATTTTCAGTAGA
       460        470        480        490        500
AATTAAACACATTAATCAACACTTGAGTAATAAAATGATCATCAACAATC
       510        520        530        540        550
TAATCATTTGGTTTACAAATTGAGAAATACTAAGGAGACTGTTTCAAAGT
       560        570        580        590        600
AAGACTTCCTATGAACTCTCTATCACCTCATATTCTTGGCACAAAATTTT
       610        620        630        640        650
ATAACATTAACATAAGAATTGTATCAAAAACATAAAATGACAGAAAATTC
                                      putative_TATA_box
       660        670        680        690 |      700
GTAGAAAATCACATTCAAGATAATAGCCTTAGCAATTCCCTTATAAACTT
       710        720        730        740        750
TGTCATCTAACATTTCCCTCTCTATTCACTCTCCTCACACTCAAACACAC
       760        770        780        790        800
ACCGTGGACTGGTTCATGCTTGCCACTTGTACCTCCCAAGAGGTTCTAGA
       810        820        830        840        850
CCCTTCATATCCTATCCTCTTCCCACGTGTCCATCTTCAATTTTACATAT
       860        870        880        890        900
ACGTCACCCTCCTCCTTAAATAACCACTCTCTTCACTTCCATCTTCTGAC
       910        920        930        940        950
TTGCAAACGCTAAACCCCCAAATCACCCCATCTTATCATCTTCTCTCTCT
       960        970        980
CTCCCTCTCTCTCCTTCTCTCGCATCAATCCATGG
```

Fig. 2

HinDIII/BglII
AAGCTTTAGA TCTCATGGGC GATGTGGGAT GTCACAATCC ACCCCCCTTA
GGGGCCCGAC GTCCTCGTCA TCACACTTCC GGCCAGGGAT TGGCTCTAAT 100
ACCATTTGTC ACATCCCGGC CCGGATCCAC CACATCTCAA GCCCGTTCCA
CCACCGTAGC ATGATATTGT CCGCTTTGGG CTTACCATTC CCTCACGGTT 200
TTGTTTTTGG GAACTCACGA GCAACTTCCT AGTGGGTCAC CCATCCTGGG
AGTGTTTAAC TTCGGAGTTC CTACGAAACC CGAAGCCAAT GAGCTCCCAA 300
AAGGTCTCGT GCTAAGTAGG GATGAGAATA TACATTTAAG GATTACTCCC
CTGGGCGATG TGGGATGTCA CAATTTGGGT AAGAAAATGA CAAGATCAAA 400
TTAAAACTGT CAAGTTTTAT GCAAATTTGA AAAACAATTA CAAAATCTTA
AGGAAAGTAT AACATTAGTG CTTTTTTTTT TGTTCCAAGA AGCATTAACA 500
TACAATTTGT TATGATATAT TAATATGCAA TGATTTAAA CATTAATGCA
TTTTTTTTC ATTAATCCCT CCCTTCAAAT ATGCATAGAA TTTAATGTAT 600
ACATTAAAAC TTTAATTAGG GGTGTTTTAG GCATCTAAAA AAATGCAAAA
TGTGTAAAGG CAAATAGAAT TAATGACTTT GCTTATGTGG AGCCTAGTCA 700
TTAGGTTTTA TTTAGATAAA AAGACTATGT CAGGTTTTAT GTAAAGAAAC
TTGAGTTTCA AGAGCTAAAG TCATATTTTC AGTAGAAATT AAACACATTA 800
ATCAACACTT GAGTAATAAA ATGATCATCA ACAATCTAAT CATTTGGTTT
ACAAATTGAG AAATACTAAG GAGACTGTTT CAAAGTAAGA CTTCCTATGA 900
ACTCTCTATC ACCTCATATT CTTGGCACAA AATTTTATAA CATTAACATA
AGAATTGTAT CAACAACATA AAATGGCAGA AAGTTCGTAG AAAATCACAT 1000
TCAAGATAAT AGCCTTAGCA ATTCCTTAT AAACCCCGT TTCTCTTCTT
CCCTCTTCCT CTTATTCTCG TCTTTCAACT CACCTAGGTC GACAACACTC 1100
ACTCCTCTCT CAGCCAGACC TTCTTCTTTG GAGGGTTGGC TCTTTCTTCT
TCGTTCGTTC CTTCCTTCCT TCATTCATTC TCCTCTCTTT CATCCAAGGT 1200
TTGTTTCTTC CTTCCCTTTT TTACCAAATC TTCTCACTTC CCTTACATTT
TTCATCTGGG GTATCGTTCT TTTCCCAAAT TATGCTGCTT TCGTCTCTCA 1300
TTTATCTACT TTATTGCTTT TAACTCATTT TCCCTTATGC GGTTCTTCAA
TTTTGGCTGA TCTTGCTGTT TGTTTTGGAA TTCTGTTTTA ATCGCCCTGG 1400
ATCCGAGGTT TTTGTTCGTA CAATCTACCT AGATTCTTTC TGTTTGTTTG
CTGATCTGAA ATTTTCCATT TGGGTTTTGA TTGTCTGTGC TTACGGAACT 1500
GAGATCTAGG ATTTGGAGTT GTGTACCTTT TTATTTCTGC ATGCAATTCT
GTAATCCTGC ATAGCTGGAT GGCTTTCTGT TGATTAGTGC ATGCTTTGTT 1600
TAGGACGAAC TGACTTGGAT TTTTCGTTGT CGATCTGTTC TATTTTTTGT
TTTGCTGTTC TGGTTCATGC TTGGAATGAT TTAGTTGCTT TGTAAATTGT 1700
ACACTCTGCT TTTGTGTTAG TTCACGTAGC TTCTCGATCT GAAATTGGAT
ATGGTTAGAG TTTATGGTCA GCTTGTGATC TTGCATTATG CAAAAATTGG 1800
AACTTAATC CTTTTCATTT GTAAGATCTT TAAGATATCT GATTACCTGG
TTGATTTTTT TGTGTCTGGA TTATTTATT TGTTTTGAAA GTAGTTTGTT 1900
GGTTCTTCCT GTATTATTTG CTGAATCGGG ATGATCAATT ATATGACGTG
AATTTATGGA ATGTAAATGA ATGGTTTAAG AGATTGCTTT GTGTGGCTTA 2000
TTTATTCAAT TTCTATTTTT ACATCGTTTT GTGCAGGTTT TGAAAAAAAA
GGGCCCATGG

Fig. 3

```
         10        20        30        40        50
CGCCGTCGCTGAACTCGATCCGTGGCGCAGTCGAATGCCAGACCCAACTC
         60        70        80        90       100
AAAACCGAGTTTTTCCATTTTTAATTTTTTAAGTTTTTAATTATATAAAA
        110       120       130       140       150
ATATTTTTTAATTATTTACATACTTTTAGTTTCACATGGTAATGTTTAA
        160       170       180       190       200
TTAGATTTGTGGGACCCATTTATGTGTCACGTCAGCCCGTAACAGAATTT
        210       220       230       240       250
TTTACGAAATTATCACATTGATTTGCGACATCTATTTTCAGAGACTACAT
        260       270       280       290       300
TGATTGGTTTTTAATTTTATAAACCATCTTAATGAAGTATGTCAATTTTA
        310       320       330       340       350
AAGATCATTTATTACAAAAACCCTTTATTTAATTTTATATTGAAATACTA
        360       370       380       390       400
AAATATGATAAAATGTACTCGAATAGTTTAGTAGATAGGGTGGTGTTATT
        410       420       430       440       450
TAGATACTTATTATTTTATTTTTATACATACTCTTCTTAATTTCTAATCA
        460       470       480       490       500
GAAAATTGAATTAATAAAAAAATATCAATGAAAAATAATTTAACAAAAAT
        510       520       530       540       550
GTACAAAAATACAGAATGAACGTGGAAATAGCACTATACCCTAGTAGATA
        560       570       580       590       600
TTGGATAAAATATATTATGGGTTTAAAATTGAAAAAATATATGTGGTTTC
        610       620       630       640       650
GAGCCATACGGGCCCGGGAATGACCGACTGTTGCAGTGCCTCTGGCCAAT
        660       670       680       690       700
CCCAACTCGACAACGTTTTGACGAAACCACTCTGGTTTTCCAACCCCAC
                             putative_TATA_box
        710       720       730   |   740       750
CCATTTCACTCTTACAGCGGTTTTGAAATATCCTATAAATATATCATACA
        760       770       780       790       800
AATACAACAGAGAAATTTTTTTTTTTGTCAAAATATACAACAGAGAATTG
                  GAGA_box                 GAGA_box
        810       820       830       840       850
AGTCACTCATATATAGACAGAGAAGGAGAGAGACCAGACCCCTACCTTAG
        860       870       880       890       900
AGAGAGAGAGAGAGCAGAAGCCATCTGTGTGTCAACTGGTTCTTTCTCTC
        910       920       930       940       950
CCATTTTCTTGGTTTCTTGGTGGGATTTCTGGTTTCTCTAAACTAAGAG
        960       970       980       990      1000
ATCAGTTCAGCAGGAACAACCGTATATATATTACTAGGATTATTAATTAT
       1010      1020      1030
TTATTTATAATAATAAATAATTGTTAGAGAGACCATGG
```

Fig. 4

APPLE PROMOTERS FOR EXPRESSION OF TRANSGENES IN PLANTS

This application claims priority to U.S. Provisional application Ser. No. 60/132,124, filed Apr. 30, 1999, expressly incorporated by reference herein.

Portions of this work were funded by the National Institute of Standards and Technology (NIST) Cooperative Agreement Number 70NANB7H3015. Accordingly, the United States Government has certain rights in this invention.

FIELD OF THE INVENTION

The present invention relates to novel apple fruit-associated and Thi 1.3:actin fusion promoters, and to heterologous nucleic acid constructs, vectors, kits, and transformation methods employing such promoters. The invention further relates to transgenic plant cells and plants transformed with heterologous nucleic acid constructs comprising an apple fruit-associated or Thi 1.3:actin fusion promoter.

REFERENCES

Adams, D. O., and Yang, S. F., *Plant Physiology* 70:117–123 (1977).
An, G, et al., *EMBO J*. 4:277–284 (1985).
Atkinson et al., *Plant Mol. Biol.* 38:449–560, 1998.
Ausubel, F M, et al., in CURRENT PROTOCOLS IN MOLECULAR BIOLOGY, John Wiley and Sons, Inc., Media, Pa. (1992).
Ayub, R., et al., *Nature Biotechnology* 14:862–866 (1996).
Altschul, et al., *Nucl. Acids Res.* 25(17) 3389–3402 (1997).
Becker, D., et al., Plant Mol. Biol. 20:1195–1197 (1992).
Belanger F C, et al., *Plant Mol. Biol.* 29: 809–821, 1995.
Bellini, C., et al., *Bio/Technology* 7(5):503–508 (1989).
Bestwick, et al., 1995; U.S. Pat. No. 5,859,330
Brunke, K J and Wilson, S L, European Patent Publication No. 0 559 603 A2, published Sep. 08, 1993.
Clendennen and May, *Plant Physiol* 115(2):463–9, 1997
Comai, L., and Coning, A. J., U.S. Pat. No. 5,187,267, issued Feb. 16, 1993.
Cordes, S, et al., *The Plant Cell* 1:1025–1034, 1989.
Doerner et al., *Nature* 380: 520–523, 1996.
Dong, J. Z., et al., *Bio/Technology* 9:858–863 (1991).
Fang, G, and Grumet, R, *Plant Cell Rep.* 9:160–164 (1990).
Ferro, A, et al., U.S. Pat. No. 5,416,250, issued May 16, 1995.
Fils-Lycaon et al., Plant Physiol. 111:269–273, 1996.
Fujioka et al., *Plant Cell* 9: 1951–62, 1997.
Good et al., *Plant Mol. Biol.* 26:781–790, 1994.
Gonsalves, C, et al., *J Amer. Soc. Hort. Sci.* 119:345–355 (1994).
Hooykaas, P J, and Schilperoot, R A, in TRENDS IN BIOCHEMICAL SCIENCES, International Union of Biochemistry and Elsevier Science Publishers, v.10(8):307–309 (1985).
Houck, C M and Pear, J R, U.S. Pat. No. 4,943,674, issued Jul. 24, 1990.
Hughes, J A, et al., *J. Bact.* 169:3625–3632 (1987).
Jacob-Wilk, D. et al., *Plant Mol. Biol.* 35: 661–666, 1997.
Jefferson, R A, et al., *EMBO J*: 6:3901 (1987a).
Jefferson, R A, *Plant Mol. Biol. Rep.* 5:387 (1987b).
Jefferson, R A, *Nature* 342(6251) 837–838, 1989).
Klein, T. M., et al., *PNAS USA* 85(22):8502–8505 (1988).
Knee M. POME FRUITS In; Seymour et al., Eds., BIOCHEMISTRY OF FRUIT RIPENING, p 325–346, Chapman & Hall, London, 1993.
Lay-Yee, 1993, *Plant Physiol.* 103: 1017)
Lee S A, et al. *Plant Physiol.* 103(3): 1017, 1993.
Ledger and Gardner, *Plant Mol. Biol.* 25:877–886, 1994.
Leisner, S. M., and Gelvin, S. B., *Proc. Natl. Acad. Sci. USA* 85(8):2553–2557 (1988).
Li et al., *Science* 272: 398–401, 1996.
Lin, E., et al., *Plant Mol. Biol.* 23:489–499 (1993).
Maniatis, T et al., in MOLECULAR CLONING: A LABORATORY MANUAL, Cold Spring Harbor Laboratory, Cold Spring Harbor, N.Y. (1982).
Mathews H et al., *Plant Cell Rep.*, 14:471–476, 1995a.
Mathews H et al., *In vitro* 31:36–43, 1995a.
McCormick et a, *Plant Cell Reports* 5:81–84, 1986.
Miki, B L A, et al., PLANT DNA INFECTIOUS AGENTS (Hohn, T., et al., Eds.) Springer-Verlag, Vienna, Austria, pp. 249–265 (1987).
Ni, M et al., *Plant J*. 7:661–676 (1995).
Norelli et al., *HortScience*, 31:1026–1027, 1996.
Picton S, et al., *Plant Physiology* 103(4):1471–1472 (1993).
Ranier et al., *Bio/Technology* 8:33–38, 1990.
Ribeiro A et al., *Plant J* 10:361–8, 1996.
Robinson H L and Torres, Calif., *Sem. Immunol.* 9:271–282, 1997.
Rogers S, U.S. Pat. No. 5,034,322, issued Jul. 23, 1991.
Sagi et al., *Bio/Technology* 5:481–485, 1995.
Sambrook J, et al., in MOLECULAR CLONING: A LABORATORY MANUAL, Cold Spring Harbor Laboratory Press, Cold Spring Harbor, N.Y., Vol. 2 (1989).
Sung and An, 5th International Congress of Plant Molecular Biology, Singapore, Poster Abstract #403, 1997; GenBank accession number U78948.
Tattersall D B, et al., *Plant Physiol* 114: 759–69 (1997).
Valles M P and Lasa, J M, *Plant Cell Rep.* 13:145–148 (1994).
Van Haaren M J J, et al., *Plant Mol. Bio.* 21:625–640 (1993).
Verdaguer et al., *Plant Mol Biol.* 37:1055–1067 (1998).
Xu R, et al., *Plant Mol. Biol.* 31:1117–1127(1996).
Yao J et al., *J. Amer. Hort. Sci.* 124(1):8–13, 1999.
Yoshioka K, et al., *Jpn. J. Breeding* 42(2):278–285 (1992).
Zhu Q, et al., *Plant Cell* 7:1681–1689 (1995).

BACKGROUND OF THE INVENTION

Transcriptional regulatory sequences or promoters that regulate gene expression in plants are essential elements of plant genetic engineering. Several examples of promoters useful for the expression of heterologous genes in plants are now available (Zhu, et al., 1995; Ni, et al., 1995).

Most promoters are from about 500–1500 bases. Promoters for expressing a heterologous gene sequence in plants can be derived from plant DNA, e.g., the cauliflower heat shock protein 80 (hsp80, Brunke and Wilson, 1993; U.S. Pat. No. 5,612,472), or from other sources, for example, plant viruses e.g., the 35S cauliflower mosaic virus promoter, or bacteria which infect plants, e.g., the nopaline synthase (nos) promoter (Rogers, 1991), the octopine synthase (ocs) promoter (Leisner and Gelvin, 1988) and the mannopine synthase (mas) promoter from Agrobacterium.

Expression of heterologous genes or selected sequences of genes in transgenic plants has typically involved the use of constitutive promoters, which drive the expression of a product throughout the plant at all times and in most tissues (e.g., hsp80), the tomato ubiquitin promoter (Picton, et al., 1993), and the raspberry E4 promoter (U.S. Pat. Nos. 5,783,393; and 5,783,394).

A limited number of inducible and/or tissue specific promoters are known. Promoters that provide fruit-specific expression include the E4 and E8 promoter from tomato (Cordes, et al., 1989; Bestwick, et al., 1995; U.S. Pat. No. 5, 859,330). Another fruit-specific promoter is the tomato 2AII gene promoter. It has been demonstrated that nucleic acid sequences placed under the regulatory control of the 5' non-coding region of the tomato 2AII gene (Van Haaren, 1993) are preferentially transcribed in developing fruit tissue. Fruit specific regulation of the kiwifruit actinidin promoter has been reported to be conserved in transgenic petunia plants (Lin, et al., 1993).

Differential screening has been used to identify abundant transcripts in developing and ripening fruit. In banana, for example, a cDNA clone encoding a putative thaumatin-like protein is identified as among the most abundant transcripts in ripening fruit, and in kiwifruit a metallothionein-like transcript is identified as very abundant in ripening fruit (Clendennen and May, 1997; Ledger and Gardner, 1994). Abundant transcripts have also been identified in the fruit of grape, cherry, and apple (Fils-Lycaon et al., 1996; Lee et al., 1993).

A transcript was previously identified in Golden Delicious apple (GenBank L15194; Lee, Gardner, and Lay-Yee, 1993, *Plant Physiol.* 103: 1017) that is abundant in fruit and shows sequence similarity to an auxin-repressed protein (ARP) of unknown function from strawberry.

Apple is a fruit which has been the subject of a great deal of study over the past several decades (Knee, 1993). Ethylene reduction is desired by packers and shippers in order to maintain apples from over-ripening and rotting. Refrigeration, high concentrations of $CO_2$ and low concentrations of $O_2$ are currently being employed to reduce the harmful effects of ethylene during storage. Such methods suffer from the disadvantages that fruits picked at preclimacteric stages (prior to full ripening) respond better to controlled atmosphere conditions than those at mature stages and many varieties of apple suffer from chilling injury and physiological disorders due to controlled atmosphere conditions, rendering them unmarketable.

Ethylene is a plant hormone influencing many aspects of plant growth and development, and is known to play a major role in the ripening process in fruits and vegetables. A large amount of ethylene is also produced following trauma caused by chemicals, temperature extremes, water stress, ultraviolet light, insect damage, disease, or mechanical wounding. In some tissues, exposure to only a small amount of ethylene may cause an avalanche of ethylene production in adjacent plants or plant tissues such as fresh produce. This autocatalytic effect can be very pronounced and lead to loss of fruit quality during transportation and storage.

In plants, the ethylene biosynthetic pathway is an offshoot of the methionine recycling pathway wherein S-adenosylmethionine (SAM) is converted to aminocyclopropane-1-carboxylic acid (ACC) by the enzyme ACC synthase. A bacterial enzyme, S-adenosyl methionine hydrolase (SAMase), not normally present in plant tissue, hydrolyzes SAM, thereby slowing the production of the metabolic precursor of ethylene, ACC.

Stable integration and expression of SAMase in the cells of soft fruits and vegetables has resulted in reduced ethylene production. (See, e.g., Good et al., 1994; Mathews et al., 1995a; Mathews et al., 1995b.) Aminocyclopropane-l-carboxylic acid (ACC)-oxidase and polygalacturonase (PG) promoters have also been isolated from apple and their effects on fruit-specific gene expression evaluated (Atkinson et al., 1998).

A need exists for plant promoters that are selectively functional in particular plant tissues or types of plants and which are capable of providing expression of heterologous genes in the cells of such tissues and plants.

SUMMARY OF THE INVENTION

Applicants have identified novel fruit-associated apple promoters, designated in the present application as "Thi-1" and "MADS2", respectively.

Applicants have also constructed a fusion promoter, designated Thi 1.3:actin, which comprises a 1.3 kb Thi-1 promoter sequence component and a melon actin promoter sequence component.

In one embodiment, the invention provides an isolated nucleic acid molecule comprising an apple fruit-associated "Thi-1" promoter, a functional portion thereof, or a sequence complementary to it which remains stably bound to the isolated nucleic acid sequence under at least moderate, and optionally, under high stringency conditions.

In exemplary aspects of this embodiment 1.3 kb and 975 bp Thi-1 promoters are provided, as presented in FIG. 1 (SEQ ID NO: 1) and FIG. 2 (SEQ ID NO:2), respectively.

In another embodiment, the invention provides an isolated nucleic acid molecule comprising an apple Thi 1.3:actin fusion promoter or a functional portion thereof, or a sequence complementary to it which remains stably bound to the isolated nucleic acid sequence under at least moderate, and optionally, under high stringency conditions.

An exemplary Thi 1.3:actin fusion promoter has the sequence presented in FIG. 3 (SEQ ID NO:3).

In another embodiment, the invention provides an isolated nucleic acid molecule comprising an apple fruit-associated MADS2 promoter or a functional portion thereof, or a sequence complementary to it which remains stably bound to the isolated nucleic acid sequence under at least moderate, and optionally, under high stringency conditions.

An exemplary apple fruit-associated MADS2 promoter has the sequence presented in FIG. 4 (SEQ ID NO:4).

The invention also provides nucleic acid constructs having a DNA coding sequence under the transcriptional control of an apple fruit-associated or Thi 1.3:actin fusion promoter. The DNA coding sequence is typically heterologous to the promoter and operably linked to the promoter to enable expression of the encoded sequence in fruit cells.

In one respect, an apple fruit-associated or a Thi 1.3:actin fusion promoter of the present invention can be used to modulate ethylene production in transformed fruit cells and thereby alter the ripening phenotype of transgenic fruit composed of such fruit cells.

In this embodiment of the invention, the apple fruit-associated promoters and Thi 1.3:actin fusion promoter described herein are employed in a method for prolonging ripening and delaying senescence of fruit from a fruit-bearing plant. In this method, a transgenic plant containing a promoter of the present invention operably linked to a heterologous DNA coding sequence is grown to the fruit-bearing stage, at which point the heterologous DNA coding sequence is expressed in the fruit of the transgenic fruit-bearing plant.

In particular, the heterologous DNA sequence encodes a product capable of reducing ethylene biosynthesis when expressed in plant cells, e.g., S-adenosyl methionine hydrolase (SAMase), amino-cyclopropane-1-carboxylic acid (ACC) deaminase, ACC oxidase antisense molecule, ACC synthase antisense molecule, ACC oxidase cosuppression molecule, and ACC synthase cosuppression molecule. Fruit produced by these transgenic plants have a modified ripening phenotype. A modified ripening phenotype refers to an alteration of the rate of ripening (e.g., prolonged ripening and delayed senescence) of a transgenic fruit relative to corresponding (ie., non-transgenic) wild-type fruit.

In another embodiment, an apple fruit-associated or Thi 1.3:actin fusion promoter of the invention is used to control expression of a DNA coding sequence such as a pathogenesis related gene, e.g polygalacturonase inhibiting protein (PGIP), glucanase and chitinase.

Additional exemplary DNA coding sequences include, but are not limited to sequences which encode, thaumatin, sucrose phosphate synthase, invertase, lycopene cyclase, antimicrobial peptides, invertase, antisense polyphenol oxidase, antisense polyphenol peroxidase, and antisense pectate lyase.

The invention further includes a method for producing a transgenic plant such as a fruit-bearing plant. In this method, a chimeric gene, typically carried in an expression vector allowing for selection in plant cells, is introduced into progenitor cells of selected plant. These progenitor cells are then grown to produce a transgenic plant bearing fruit.

The methods and results described herein demonstrate tissue-associated regulation of gene expression in transgenic plants. The tissue-associated promoters of the present invention include a DNA sequence that regulates transcription of a heterologous nucleic acid coding sequence to which it is operably linked.

The present invention also includes the use of any of the above promoters in plant transformation vectors. Such vectors can be used in any plant cell transformation method, including Agrobacterium-based methods, electroporation, microinjection, and microprojectile bombardment. These vectors may form part of a plant transformation kit. Other components of the kit may include, but are not limited to, reagents useful for plant cell transformation.

In another embodiment, the invention includes a plant cell, plant tissue, transgenic plant, fruit cell, whole fruit, seeds or calli containing any of the above-described promoters, chimeric genes and the corresponding expressed gene products.

These and other objects and features of the invention will become more fully apparent when the following detailed description is read in conjunction with the accompanying figures and examples.

BRIEF DESCRIPTION OF THE FIGURES

FIG. 1 is a single-stranded depiction of a modified apple fruit-associated Thi-1(1.3 kb) promoter sequence (SEQ ID NO: 1), as provided inpAG162. A HindIII restriction site (AAGCTT) was engineered into the 5' end and an NcoI site (CCATGG) engineered at the start codon (underlined). A putative TATA-box has been identified at nucleotides 1028–1033.

FIG. 2 is a single-stranded depiction of a modified apple fruit-associated Thi-1(975 bp) promoter sequence (SEQ ID NO:2), as provided in pAG 162a. A HindIII restriction site (AAGCTT) was engineered into the 5' end and an NcoI site (CCATGG) engineered at the start codon (underlined). A putative TATA-box has been identified at nucleotides 692–697.

FIG. 3 is a single-stranded depiction of the complete nucleotide sequence of a Fuji Thi 1.3-Actin fusion promoter (SEQ ID NO:3), as provided in pAG-752. Restriction sites used in subcloning are underlined, HinDIII and BgIII at the 5' end and NcoI containing the translational start codon ATG at the 3' end. The TATA-box delineating the fusion between the Fuji Thi 1.3 promoter and the melon actin promoter is bolded and underlined.

FIG. 4 is a single-stranded depiction of a modified apple fruit-associated MADS2 promoter sequence (SEQ ID NO:4), as provided in pAG168. A putative TATA-box is identified at nucleotides 734–739 and "GAGA" boxes, consisting of GA repeats are also identified in the 5' UTR region. The start codon (ATG) is underlined, and surrounded by an NcoI site (CCATGG).

DETAILED DESCRIPTION OF THE INVENTION

I. Definitions

As used herein, the term "polynucleotide" refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded ribonucleic acids (RNA) and deoxyribonucleic acids (DNA), and may include polymers having backbone modifications such methylphosphonate linkages.

A nucleic acid may be double stranded, single stranded, or contain portions of both double stranded and single stranded sequence. The depiction of a single strand also defines the sequence of the other strand and thus also includes the complement of the sequence which is depicted.

As used herein, the term "recombinant nucleic acid" refers to nucleic acid, originally formed in vitro, in general, by the manipulation of nucleic acid by endonucleases, in a form not normally found in nature.

As used herein, the terms "chimeric gene", "chimeric gene construct" and "chimeric nucleic acid construct" are used interchangeably and refer to recombinant nucleic acid sequences which comprise a DNA coding sequence and control sequences required for expression of the coding sequence in a plant cell.

As used herein, the term "transgene", refers to a non-native nucleic acid sequence, usually encoding a polypeptide, introduced into a host genome using recombinant DNA techniques.

As used herein, the term "regulatable promoter" refers to any promoter whose activity is affected by specific environmental or developmental conditions (e.g., a tomato E4 or E8 promoter).

As used herein, the term "constitutive promoter" refers to any promoter that directs RNA production in many or all tissues of a plant transformant at most times.

As used herein, the term "tissue-associated promoter" refers to any promoter which directs RNA synthesis at higher levels in particular types of cells and tissues, e.g., an apple fruit-associated promoter directs RNA synthesis at higher levels in apple fruit, relative to expression levels in apple leaves.

As used herein, the terms "promoter" or "promoter segment" refer to a sequence of DNA that functions in a promoter disclosed herein to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

By "plant promoter" is meant a promoter or promoter region (as defined above), which in its native form, is derived from plant genomic DNA. The apple fruit-associated and apple Thi 1.3:actin fusion promoters of the present invention are plant promoters.

As used herein, "promoter strength" refers to the level of promoter-regulated expression of a chimeric or heterologous gene in a plant tissue or tissues, relative to a suitable standard (e.g., a fruit-associated promoter from a particular plant, such as apple, versus a control or standard gene promoter, for example, the 35S CaMV promoter or the CsVMV promoter (Cassava Vein Mosaic Virus promoter, Verdaguer et al., 1998). Expression levels can be measured by linking the promoter to a suitable reporter gene such as GUS (β-glucuronidase). Expression of the reporter gene can be easily measured by fluorometric, spectrophotometric or histochemical assays (Jefferson, et al., 1987a; Jefferson, 1987b; Jefferson, R A, 1989).

A nucleic acid sequence is "heterologous" with respect to a control sequence (i.e. promoter or enhancer) when it does not function in nature to regulate the same gene the expression of which it is currently regulating. Generally, heterologous nucleic acid constructs are introduced into the cell or part of the genome in which they are present, and have been added to the cell, by transfection, microinjection, electroporation, or the like. The sequences may contain a control sequence/DNA coding sequence combination that is the same as, or different from a control sequence/DNA coding sequence combination found in the native plant.

As used herein, the term "operably linked" relative to a recombinant DNA construct or vector means nucleotide components of the recombinant DNA construct or vector are in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

The term "gene", may be used interchangeably herein with the term "nucleic acid coding sequence", and the term "structural gene" which means a DNA coding region.

As used herein, the term "sequence identity" means nucleic acid or amino acid sequence identity in two or more aligned sequences, aligned using a sequence alignment program. Sequence searches are preferably carried out using the BLASTN program when evaluating the of a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. [See, Altschul, et al., 1997.]

The term "% homology" is used interchangeably herein with the term "% identity" herein and refers to the level of identity between two sequences, ie. 70% homology means the same thing as 70% sequence identity as determined by a defined algorithm, and accordingly a homologue of a given sequence has at least about 70%, preferably about 80%, more preferably about 85%, even more preferably about 90% sequence identity over a length of the given sequence.

A preferred alignment of selected sequences in order to determine "% identity" between two or more sequences, is performed using the CLUSTAL-W program in MacVector version 6.5, operated with default parameters, including an open gap penalty of 10.0, an extended gap penalty of 0.1, and a BLOSUM 30 similarity matrix.

A nucleic acid sequence is considered to be "selectively hybridizable" to a reference nucleic acid sequence if the two sequences specifically hybridize to one another under moderate stringency hybridization and wash conditions. Exemplary conditions include hybridization conducted as described in the Bio-Rad Labs ZetaProbe manual (Bio-Rad Labs, Hercules, Calif.), expressly incorporated by reference herein. For example, hybridization is conducted in 1 mM EDTA, 0.25 M $Na_2HPO_4$ and 7% SDS at 60° C., followed by washing in 1 mM EDTA, 40 mM $NaPO_4$, 5% SDS, and 1 mM EDTA, 40 mM $NaPO_4$, 1% SDS. Hybridization conditions are further recited in Ausubel F M et al., 1993, expressly incorporated by reference herein.

As used herein, the term "expression" refers to the process by which a polypeptide is produced based on the nucleic acid sequence of a gene. The process includes both transcription and translation.

As used herein, the terms "transformed", "stably transformed" or "transgenic" refer to a plant cell that has a non-native (heterologous) nucleic acid sequence integrated into its genome which is maintained through two or more generations.

As used herein, the term "modulate" refers to a change in biological activity. Modulation may relate to an increase or a decrease in biological activity, binding characteristics, or any other biological, functional, or immunological property of the molecule.

As used herein, the term "ethylene regulated", refers to regulation which is induced by changes in ethylene concentration in the plant. For example, promoter activity which occurs or primarily occurs, during later stages of fruit development and/or early stages of fruit ripening, is said to be ethylene regulated.

As used herein, a "plant cell" refers to any cell derived from a plant, including undifferentiated tissue (e.g., callus) as well as plant seeds, pollen, progagules and embryos.

II. Apple Promoter Isolation

Differential screening has been used to identify abundant transcripts in developing and ripening fruit. In banana, for example, a cDNA clone encoding a putative thaumatin-like protein was identified as among the most abundant transcripts in ripening fruit, and in kiwifruit a metallothionein-like transcript was identified as very abundant in ripening fruit (Clendennen and May, 1997; Ledger and Gardner, 1995). Abundant transcripts have also been identified in the fruit of grape, cherry, and apple (Tattersall et al., 1997; Fils-Lycaon et al., 1996; Lee et al., 1993).

Random amplification of products ("RAP") screening is a PCR-based technique that allows the rapid isolation of abundant transcripts from a PCR-accessible cDNA library constructed from an mRNA of interest.

A. Construction Of PCR-Accessible cDNA Libraries

PCR accessible cDNA libraries were made using Clontech's Marathon cDNA Amplification Kit [Clontech Laboratories, Inc.: Palo Alto, Calif. 94303-4230], following the manufacturer's protocol. Briefly, after first and second-strand cDNA synthesis, adaptors were ligated to the polished ends of the double-stranded cDNA. This cDNA library served as a PCR-accessible cDNA library for rapid amplification of cDNA 5' or 3' ends.

After the libraries were constructed, modified adaptors were ligated to the digested DNA fragments, such that the adaptor thereby defines one end of the PCR template. A pair of nested gene specific primers and a pair of nested adaptor primers were used to amplify a specific product or products. A chemical modification of the adaptor, as well as the use of touchdown PCR parameters, minimized amplification of non-specific products.

Touchdown PCR parameters are thermal cycling parameters in which the annealing temperature is initially very high, and gradually decreases during subsequent cycles. Reagents and protocols for touchdown PCR are commercially available.

Upstream sequences associated with differentially expressed apple mRNAs were isolated in a series of steps. Oligonucleotide primers were designed based on the differential display fragments selectively expressed in a particular fruit tissue or fruit tissue at a particular stage of development (i.e., complementary to the 5' end of the fragment), and used to walk upstream in a PCR-accessible apple genomic library.

B. RAP Screening

A PCR-accessible cDNA library was constructed using Clontech's Marathon cDNA Amplification Kit, following the manufacturer's protocol, as set forth above [Clontech Laboratories, Inc., Palo Alto, Calif. 94303-4230]. Amplification products representing high-abundance transcripts in the mRNA pool were identified by hybridization with a labeled total cDNA probe. mRNA was isolated from particular tissues, reverse transcribed into double-stranded cDNA, blunt-ended and adaptors ligated to the double-stranded cDNA. The cDNA library was serially diluted 10-fold, at least ten times, in order to reduce non-abundant transcripts to undetectable levels. Each serial dilution was used as a template in replicated PCR reactions. Products were amplified using an oligonucleotide complimentary to the adaptor sequence and a cDNA synthesis primer for random amplification. The products of the PCR reactions were separated by agarose gel electrophoresis and analyzed by Southern blot, and visualized on an ethidium bromide-stained gel. The blots were probed with radiolabeled first-strand cDNA, from the same MRNA used to construct the library. Amplification fragments which hybridize strongly to the labeled cDNA probe represent abundant transcripts in the tissue that served as the source for RNA extraction. These fragments were cloned and their expression pattern further analyzed by Northern hybridization.

III. Apple Fruit-Associated Thi-1 Promoters cDNA libraries were generated using RNA isolated from post-harvest Fuji apple fruit. The libraries were made using Clontech's Marathon cDNA Amplification Kit (Clontech, Palo Alto, Calif.), and served as PCR-accessible libraries for random amplification of products (RAP) and screening by hybridization (post harvest fruit library).

Using the RAP technique, a cDNA fragment was identified as being abundantly expressed in Fuji apple fruit (post harvest). The Fuji apple cDNA fragment (LIB7) was cloned, sequenced and found to exhibit nucleotide sequence homology to plant thiamine biosynthetic enzymes (Thi).

Thiamine or vitamin B-1, is an essential constituent of all cells since it is a cofactor for two enzyme complexes involved in the citric acid cycle, pyruvate dehydrogenase and alpha-ketoglutarate dehydrogenase. Plant thiamine biosynthetic enzymes (Thi) are known to exist in higher plants, however, the biosynthetic pathway for thiamine in plants has not been well characterized.

A Thi-1 gene homologous to yeast and plant genes encoding an enzyme belonging to the pathway of thiamine biosynthesis has been cloned from maturing citrus fruit, and the expression of the gene shown to gradually increase in the peel during natural fruit maturation and in response to ethylene (Jacob-Wilk, 1997; GenBank Accession Number Z82983).

Two cDNAs representing members of the maize Thi 1 gene family shown to be located in a plastid membrane fraction, have also been cloned and characterized. (Belanger, F C et al., 1995)

A cDNA clone, pAgthi 1, encoding a gene product involved in thiazole biosynthesis, was isolated from a library made from poly(A) RNA from actinorhizal nodules of *Alnus glutinosa* by differential screening with nodule and root cDNA, respectively. The corresponding gene, agthil, was shown to be expressed at high levels in nodules and shoot tips of *A. glutinosa*, while having low expression levels in roots, flowers, and developing fruits. (Ribeiro A, et al., 1996; GenBank Accession Number X97434)

The Fuji apple transcript was found to be very abundant in fruit, detectable in leaf tissue, and almost undetectable in root and ovary by Northern blot analysis. Use of the fragment as a probe on Fuji and Gala genomic Southern blots indicated two similar copies of Thi in both the Fuji and Gala apple genomes. (See Example 1.)

The Thi transcript present in Fuji apple fruit was determined to be encoded by Thi-1, and Thi-1 sequence-specific primers were designed that preferentially amplify upstream sequences associated with the Thi-1 gene, and used to walk upstream in a PCR-accessible Fuji apple genomic library. 1.2 and 1.0 kb products were amplified from PCR-accessible Fuji genomic libraries, assembled as a contiguous sequence, and the assembled sequence used to design primers for amplification of the complete Thi-1 upstream promoter sequence directly from Fuji genomic DNA.

1.3kb (SEQ ID NO: 1, FIG. 1) and 975 bp (SEQ ID NO:2, FIG. 2) Thi-1 promoters were isolated and characterized. The nucleotide sequence of the 1.3 kb fragment was found to have nucleotide sequence homology to 5S ribosomal RNA genes, while the same 5S region was removed from the 5' end of the 975 bp fragment. The 1.3 kb Thi-1 promoter sequence was also fused to a melon actin promoter at the TATA-box, resulting in a hybrid fusion promoter construct designated, "Thi 1.3:actin".

The amplified Thi-1 promoters were digested to produce the appropriate cohesive ends and cloned into compatible sites in a reporter gene construct, comprised of the promoter translationally fused with GUS and containing the nos3' terminator. The resulting constructs were designated pAG162, pAG162a and pAG752, respectively.

A basic BLASTN search of non-redundant nucleic acid sequence databases through NCBI, which can be carried out using the search capabilities of the NIH website, revealed no significant matches to the 1.3 kb and 975 bp Thi-1 promoters, as presented in (SEQ ID NO:1, FIG. 1) and (SEQ ID NO:2, FIG. 2), respectively.

A. Fusion Promoter Comprising a 1.3 kb Apple Thi-1 Sequence And A Melon Actin Sequence.

The Fuji Thi 1.3 promoter was fused to a melon actin promoter at the TATA-box, as detailed in Example 2. The complete sequence of the Fuji Thi 1.3:actin fusion (SEQ ID NO:3), as it exists in pAG752 is presented in FIG. 3. HinDIII and NcoI restriction sites were engineered into the 5' and 3' ends of the promoter fragment, respectively, to aid in subcloning.

IV. Apple Fruit-Associated MADS2 Promoter cDNA libraries were generated using RNA isolated from developing apple ovaries. The library was made using Clontech's Marathon cDNA Amplification Kit (Clontech, Palo Alto, Calif.), following the manufacturer's protocol.

These cDNA libraries were used for rapid amplification of 5' and 3' ends (RACE; developing fruit library).

A 5' RACE reaction was performed with adaptor-specific and a MADS2 gene-specific oligonucleotide primers, and a 5' RACE product of 400 bp isolated, cloned, and sequenced. The 5' RACE product showed homology to a known 5' UTR, MADSBOX and variable region of the MADS2 cDNA clone.

MADS2 has been identified as an ovary-specific transcript in Fuji apple (Sung and An, 1997). MADS2 is a homeobox gene, and the gene product is predicted to be involved in early fruit development. Upstream regulatory sequences associated with the MADS2 gene were isolated for use as a promoter to drive the expression of heterologous genes in the developing fruit of apple and other tree fruit. Seven MADS-box genes have been identified from apple and shown to be expressed in different parts of the fruit (Yao, J et al., 1999).

A putative translational start site was identified and MADS2-specific oligonucleotides designed to walk upstream in a PCR-accessible Fuji apple genomic library (using GenomeWalker, Clontech), resulting in isolation of 750 bp product. The 750 bp sequence was used to design primers for a second upstream walk which led to isolation of a 720 bp product, as detailed in Example 2.

The 400 bp RACE product, and the 750 bp and 720 bp GenomeWalker products were assembled as a contiguous sequence which was used to design primers to amplify the complete MADS2 upstream sequence directly from genomic DNA. A complete MADS2 promoter amplified from Fuji apple genomic DNA is presented in FIG. 4 (SEQ ID NO:4).

In order to confirm promoter activity, the MADS2 promoter was subcloned into a reporter gene construct in translational fusion with GUS and containing the nos terminator sequence and the resulting MADS2 promoter::reporter gene construct was designated pAG168.

The MADS2 promoter sequence exhibits a high A/T percentage, contains a putative TATA box and two "GAGA" boxes that are known to exist in the 5' UTR of the Fuji MADS2 cDNA. The nucleotide sequence of the MADS2 promoter, as it exists in pAG168, is presented in FIG. 4 (SEQ ID NO:4). A Basic BLASTN search of non-redundant nucleic acid sequence databases through NCBI, which can be carried out using the search capabilities of the NIH website, revealed sequence identity between the 5' UTR of the MADS2 cDNA (*Malus domestica* sequence, GenBank Accession number U78948; Sung, Yu and An, unpublished), and nucleotides 865 to 971 of the MADS2 promoter, as presented in SEQ ID NO:4.

V. Vectors For Transforming Plant Cells

The present invention further provides vectors suitable for the transformation of plants. The vectors, chimeric genes and DNA constructs of the present invention are also useful for the expression of heterologous genes. Transgenic plants, transgenic plant cells and transgenic fruit, carrying the chimeric genes of the present invention, may be a useful source of recombinantly-expressed material.

The apple fruit-associated and Thi-1 1.3:actin fusion promoters of the invention find utility in chimeric gene constructs for the fruit-associated expression of heterologous structural genes operably linked to the promoters. The methods and results described herein are directed to gene expression under the control of an apple fruit-associated or apple Thi-1 1.3:melon actin fusion promoter of the invention, in transgenic plant cells. The apple fruit-associated and Thi-1 1.3:actin fusion promoters of the invention include a region of DNA that promotes transcription of a gene operably linked thereto, in transformed plant cells.

Using known, routine DNA manipulation techniques such as those described in Sambrook et al. (1989), heterologous nucleic acid constructs can be made whereby a foreign structural DNA sequence of interest, or gene, is placed under the regulatory control of an apple fruit-associated or apple Thi-1 1.3:melon actin fusion promoter of the invention.

Techniques for the construction of expression vectors or heterologous nucleic acid constructs suitable for transformation into plants are known to those of ordinary skill in the art. (See, for example, Houck and Pear, 1990, and Becker, et al., 1992).

For expression in plants, the expression vectors of the invention may be constructed to contain an insertion site for a DNA coding sequence of interest. The transcription of such inserted DNA is then under the control of an apple fruit-associated or apple Thi-1 1.3:melon actin fusion promoter of the invention.

Such expression vectors may have single or multiple transcription termination signals at the 3' end of the DNA sequence being expressed. The expression cassette may also include, for example, (i) a DNA sequence encoding a leader peptide (e.g., to allow secretion or vacuolar targeting), (ii) translation termination signals, (iii) selectable marker genes for use in plant cells, (iv) sequences that allow for selection and propagation in a secondary host, such as an origin of replication and a selectable marker sequence.

Selectable marker genes encode a polypeptide that permits selection of transformed plant cells containing the gene by rendering the cells resistant to an amount of an antibiotic that would be toxic to non-transformed plant cells. Exemplary selectable marker genes include the neomycin phosphotransferase (nptII) resistance gene, hygromycin phosphotransferase (hpt), bromoxynil-specific nitrilase (bxn), phosphinothricin acetyltransferase enzyme (BAR) and the spectinomycin resistance gene (spt), wherein the selective agent is kanamycin, hygromycin, geneticin, the herbicide glufosinate-ammonium ("Basta") or spectinomycin, respectively.

Typical secondary hosts include bacteria and yeast. In one embodiment, the secondary host is *Escherichia coli*, the origin of replication is a coleE1-type, and the selectable marker is a gene encoding ampicillin resistance. Origin of replication and selectable marker sequences operative in secondary hosts are well known in the art and many are commercially available (e.g., Clontech, Palo Alto, Calif.; Stratagene, La Jolla, Calif.).

The vectors of the present invention are useful for fruit tissue-associated expression of nucleic acid coding sequences in plant cells. For example, a selected peptide or polypeptide coding sequence can be inserted in an expression vector of the present invention which has, e.g., a Thy-1, MADS2 or Thi 1.3:actin fusion promoter sequence. The vector is then transformed into host cells, and the host cells cultured under conditions to allow the expression of the protein coding sequence. In some cases, the expressed peptide or polypeptide is isolated from the cells. Transformed plant progenitor cells can also be used to produce transgenic plants bearing fruit.

Further, the invention includes a method for producing a transgenic fruit-bearing plant, where fruit produced by the plant has a modified phenotype. In this method a heterologous gene construct is introduced (e.g., by transformation) into progenitor cells of the plant. An exemplary heterologous gene construct is composed of (i) a DNA sequence encoding a gene product effective to modify a phenotypic characteristic of the plant, e.g., to reduce ethylene biosynthesis in fruit produced by the plant, operably linked to (ii) an apple promoter of the invention whose expression is fruit-associated. The DNA sequence is heterologous to the promoter and the chimeric gene contains the appropriate regulatory elements necessary for expression in a plant cell. Transformed progenitor are grown to produce a transgenic plant bearing fruit. The method further includes transforming progenitor cells of the plant with a vector containing a selectable marker and the heterologous gene.

It will be understood that the vectors described herein may form part of a plant transformation kit. Other components of the kit may include, but are not limited to, reagents useful for plant cell transformation.

VI. Methods Of Transforming Plant Cells

Chimeric genes containing an apple fruit-associated or Thi 1.3:actin fusion promoter of the invention, e.g., a Thi-1, MADS2 or Thi 1.3:action fusion promoter may be transferred to plant cells by any of a number of plant transformation methodologies, including Agrobacterium-based methods [Ranier et al., 1990 (rice); McCormick et al., 1986 (tomato); Norelli et al., 1996 (apple)], electroporation, microinjection, and microprojectile bombardment. (See, e.g., Comai and Coning, 1993; Klein, et al., 1988; Miki, et al. 1987; Bellini, et al., 1989).

In one embodiment, chimeric genes are introduced into plants by way of a T-DNA-less Ti plasmid carried by *Agrobacterium tumefaciens*, followed by co-cultivation of the *A. tumefaciens* cells with plant cells. In such cases, vectors for use in the invention contain a selectable marker gene, T-DNA border regions from *Agrobacterium tumefaciens*, a heterologous gene of interest, and other elements as desired. Exemplary Agrobacterium transformation vectors are commercially available from Clontech (Palo Alto, Calif.) and further described by An, et al., 1985.

Other suitable vectors may be constructed using the promoters of the present invention and standard plant transformation vectors, which are available both commercially (Clontech, Palo Alto, Calif.) and from academic sources [Salk Institute, Plant Biology Labs; Texas A & M University; Waksman Institute, Rutgers, The State University of New Jersey, Piscataway, N.J.].

Another embodiment is based on microprojectile bombardment using microparticles loaded with DNA which are bombarded into the cells using "gene gun" technology. (See, e.g., Robinson, H L and Torres, Calif., 1997.)

When electroporation or microprojectile bombardment transformation techniques are utilized, the transformation vector generally contains the heterologous gene of interest and a selectable marker gene construct to determine whether the transformation event was successful.

Transformed plant cells are obtained as a result of the transformation of the plant cells with a heterologous gene construct comprising an apple fruit-associated or Thi 1.3:actin fusion promoter of the invention operably linked to a heterologous gene. The plant cells are cultured in medium containing the appropriate selection agent to identify and select for plant cells which express the chimeric gene. After plant cells that express the chimeric gene are selected, whole plants are regenerated from the transgenic plant cells. Techniques for regenerating whole plants from transformed plant cells are known in the art.

The invention further includes a method for producing a transgenic plant such as a fruit-bearing plant. In this method, a chimeric gene, typically carried in an expression vector allowing selection in plant cells, is introduced into progenitor cells of a plant. These progenitor cells are then grown to produce a transgenic plant bearing fruit.

Preferred plants suitable for transformation using an apple fruit-associated or Thi 1.3:actin fusion promoter of the invention include, but are not limited to, apple, tomato, pineapple, grape, raspberry, strawberry, kiwi fruit, avocado, melon, mango, papaya, apple, peach, pear, cherry, citrus, date palm, plantain, soybean, cotton, alfalfa, oilseed rape, flax, sugar beet, sunflower, potato, tobacco, maize, wheat, rice, nuts and lettuce.

In one exemplary embodiment, cotyledon explants of a commercial cantaloupe variety (*Cucumis Melo*, Muskmelon) are transformed according to known methods (Fang and Grumet, 1990; Valles and Lasa, 1994; Dong, et al., 1991; Gonsalves, et al., 1994; Yoshioka, et al., 1992; Ayub, et al., 1996), using the a disarmed Agrobacterium strain to introduce the above-described binary vectors into plants. The disarmed Agrobacterium strain is co-cultivated with melon cotyledon tissue explants, and primary transformants selected on the basis of their capacity to regenerate and develop roots on media containing the antibiotic, kanamycin.

In other exemplary embodiments, Agrobacterium transformation methods as described for apple, rice, tomato, apple are used to transform plant cells using an apple fruit-associated or Thi 1.3:actin fusion promoter of the invention. [See, e.g., Sagi et al., 1995 (banana); Ranier et al., 1990 (rice); McCormick et al., 1986 (tomato); and Norelli et al., 1996 (apple).]

VII. Heterologous Genes

Any structural gene of interest may be placed under the regulatory control of an apple fruit-associated or Thi 1.3:actin fusion promoter of the invention. The structural gene may encode a polypeptide of interest or other gene product.

According to the methods of the present invention, heterologous genes may be operably linked to such an apple fruit-associated or Thi 1.3:actin fusion promoter.

In one aspect, the apple fruit-associated promoters of the invention are used to modulate ethylene production in transformed cells, and thereby alter the ripening and delay senescence of transgenic fruit composed of such cells.

In this embodiment of the invention, the promoters described herein are employed in a method for prolonging ripening and delaying senescence of fruit from a fruit-bearing plant, e.g., apple. In this aspect of the invention, transgenic plant cells containing the promoters of the present invention are grown to produce a transgenic plant bearing fruit.

In particular, plant cells are transformed with a heterologous nucleic acid construct encoding a product capable of reducing ethylene biosynthesis when expressed in plant cells (e.g., S-adenosyl-methionine hydrolase (SAMase, Ferro et al., 1995; Hughes et al., 1987), aminocyclopropane-l-carboxylic acid (ACC) deaminase, ACC oxidase antisense molecule, ACC synthase antisense molecule, ACC oxidase cosuppression molecule, ACC synthase cosuppression molecule), which is under the control of an apple promoter of the invention. Fruit produced by these transgenic plants has a modified ripening phenotype, as described in co-owned U.S. Pat. Nos. 5,859,330; 5,783,394; 5,783,393; 5,723,746; 5,589,623; 5,416,250 and 5,750,864, expressly incorporated by reference herein.

A modified ripening phenotype refers to an alteration in the rate of ripening; characterized by an increased ripening time course, or prolonged ripening and the delayed senescence of, a transgenic fruit relative to corresponding (i.e., non-transgenic) wild-type fruit.

In another aspect, the apple fruit-associated promoters of the invention are used to increase the resistance of a plant to pathogens. In such cases, the nucleic acid coding sequence can correspond to a pathogenesis related gene, such as polygalacturonase inhibiting protein (PGIP), glucanase or chitinase.

In a further aspect, nucleic acid coding sequences which are placed under the control of an apple fruit-associated or Thi 1.3:actin fusion promoter of the invention include sequences which affect: (i) flavor (e.g, thaumatin; GenBank); (ii) pigmentation (e.g, products that modify lycopene synthesis, such as lycopene cyclase; GenBank); (iii) enzymes or other catalytic products (such as, ribozymes or catalytic antibodies) that modify plant cell processes; (iv) enzymes that inhibit degradation of ripened fruit (e.g., antisense polyphenol oxidase and antisense polyphenol peroxidase (to inhibit browning) and antisense pectate lyase (to inhibit softening); (vi) antimicrobial peptides, (vii) sucrose accumulating genes, such as the sucrose phosphate synthase gene (GENBANK) and (viii) genes which affect the metabolism of sucrose (e.g, invertase).

VIII. Identification And Evaluation Of Transformants

Following transformation, transgenic plant cells are assayed for expression of a transgene which is operably linked to an apple fruit-associated or Thi 1.3:actin fusion promoter of the invention. Transgenic plant cells may be initially selected by their ability to grow in the presence of a selective agent, such as the aminoglycoside antibiotic, kanamycin.

Expression of a transgene may also be determined by analysis of DNA, mRNA, and protein, associated with the expression of the transgene. The assays are typically conducted using various plant tissue sources, e.g., leaves, stem, ovaries or fruit.

A. Construction Of Plant Transformation Vectors And Evaluation Of Promoter Activity Using Reporter Constructs The relative activity of apple fruit-associated and Thi 1.3:actin fusion promoters of the invention was evaluated in a transient assay system using a reporter gene, exemplified by GUS (βglucuronidase), effective to evaluate the tissue-associated regulatable expression from the promoters Expression of GUS protein is easily measured by fluorometric, spectrophotometric or histochemical assays (Jefferson, 1987a).

Recombinant nucleic acid constructs comprising; pAG162, pAG162a, pAG752 and pAG168 were prepared using the isolated promoter sequences and techniques routinely employed by those in the art, then introduced into apple plant cells by particle bombardment, as detailed below in Example 3.

The promoter activity of various GUS constructs is then evaluated in transient assays for GUS expression. Gold particle suspensions of each construct are prepared and used to bombard sterilized apple, peach and pear fruit which is immature or at various stages of maturity including fully mature ripe fruit.

B. Methods Of Detecting Apple Promoter-Driven Gene Expression

Transgenic plants are assayed for their ability to synthesize mRNA, DNA, protein, and/or for their resistance to an aminoglycoside antibiotic, e.g., kanamycin, which is associated with expression of the coding sequence that has been introduced into plant cells under the control of an apple fruit-associated or Thi 1.3:actin fusion promoter of the invention. The assays are typically conducted using various plant tissue sources, e.g., leaves, stem, or fruit Gene amplification and/or expression may be measured in a sample directly, for example, by conventional Southern blotting, Northern blotting to quantitate the transcription of mRNA, dot blotting (DNA analysis), or in situ hybridization, using an appropriately labeled probe, based on the sequences provided herein.

The following examples illustrate, but are in no way intended to limit the scope of the present invention.

MATERIALS AND METHODS

DNA Plasmids And Agrobacterium Binary Vector Construction

Biological reagents were typically obtained from the following vendors: 5' to 3' Prime, Boulder, Colo.; New England Biolabs, Beverly, Mass.; Gibco/BRL, Gaithersburg, Md.; Promega, Madison, Wis.; Clontech, Palo Alto, Calif.; and Operon, Alameda, Calif.

Specific reagents employed in the particle bombardment include BioRad Biolistic PDS-1000/He system (BioRad Laboratories, Hercules, Calif., USA), gold particles of 1.5–3.0 μm (Aldrich, Milwaukee, Wis., USA), a rupture disk: 1,100 PSI (BioRad Laboratories, Hercules, Calif., USA), stop screens of 0.685 mesh (Rumsey-Loomis, Freeville, N.Y.), macrocarriers: (Rumsey-Loomis, Freeville, N.Y.) and X-Gluc: 5-Bromo-4-chloro-3-indoyl β-D-glucuronide cyclohexylamine salt (Rose Scientific, Edmonton, Alberta, Canada).

Standard recombinant DNA techniques were employed in all constructions (Adams and Yang, 1977; Ausubel, et al., 1992; Hooykaas and Schilperoot 1985; Sambrook, et al., 1989), expressly incorporated by reference herein.

EXAMPLE 1

Library Construction For Isolation Of Apple Promoters cDNA libraries were generated using RNA isolated from developing apple ovaries and post-harvest apple fruit. Total RNA was extracted from developing and post harvest Fuji apple fruit by the following method: Tissue was frozen and ground to a powder in liquid nitrogen in the stainless steel container of a Waring Blender. The frozen tissue powder was added to RNA extraction buffer (0.5M sodium chloride; 0.1M sodium acetate; 0.05M EDTA; 1.4% (w/v) sodium dodecyl sulfate; 2% (w/v) polyvinyl pyrrolidone 40,000; 0.2% (v/v) β-mercaptoethanol). The slurry was heated to 65° C., then homogenized with two 30s pulses of a tissue homogenizer (Polytron), and incubated for 30 min at 65° C. Cell debris was removed by straining the homogenate through cheesecloth, then further cleared by the addition of 0.2 volumes of 5M potassium acetate (pH 4.8), incubation on ice for 30 min then centrifugation at 9,000×g for 10 min at 4° C. The clear supernatant was decanted into a fresh tube, and RNA was precipitated by the addition of 0.33 volumes of 10M lithium chloride and incubation overnight at −20° C. The RNA was pelleted by centrifugation at 9,000×g for 20 min at 4° C., and the resulting RNA pellet was drained and resuspended in 0.5 ml nuclease-free water. The resuspended RNA was extracted once with phenol:chloroform (1:1), then once with chloroform: isoamyl alcohol (25:1). Finally, the RNA was precipitated by the addition of 0.1 vol. 3M sodium acetate (pH5.2) and 2.5 vol. ethanol, pelleted by centrifugation (14,000×g, 10 min), drained, and resuspended in a small volume of nuclease-free water.

Poly(A)+ RNA was isolated from 600 μg total RNA using the Straight A's mRNA Isolation System Kit [Novagen, Inc., Madison, I]. The library itself was made using Clontech's Marathon cDNA Amplification Kit [Clontech, Palo Alto, Calif.] following the manufacturer's protocol. Briefly, after first and second-strand cDNA synthesis, adaptors are ligated to the polished ends of the double-stranded cDNA. This cDNA library served as a PCR-accessible library for random amplification of products (RAP) and screening by hybridization (post harvest fruit library) and also for rapid amplification of 5' and 3' ends (RACE; developing ovary library).

RAP Reactions And Hybridization

The cDNA library was serially diluted 10-fold in TE, from $10^{-1}$ to $10^{-10}$ times the original library concentration. The diluted libraries were used as a template for replicate PCR amplification reactions. Each 50 μl reaction mix was composed of: 38.5 μl water; 5 μl 10× KlenTaq reaction buffer (Clontech, Palo Alto, Calif.); 0.5 μl each primer (100 μM); 0.5 μl dNTP mix (25mM each); 5 μl diluted library; 1 μl KlenTaq DNA polymerase (Clontech). The primers used were MAR AP 1 (SEQ ID NO:5) and CSP (SEQ ID NO:6). The reactions were cycled in a Robocycler Gradient 96 Temperature Cycler with Hot Top Assembly (Stratagene, La Jolla, Calif.) using the following cycling parameters: 5 cycles [94° C., 30s; 72° C., 3min], 5 cycles [94° C. 30s; 70° C., 3min], 35 cycles [94° C., 30s; 68° C., 3min], 1 cycle [72° C., 10min], followed by a 6° C. hold. A 10 μl aliquot of each amplification reaction was separated by agarose gel electrophoresis, photographed, then transferred to nylon membrane (Nytran Plus, Schleicher and Schuell) by capillary blotting using 0.4M sodium hydroxide as the transfer fluid.

The labeled first-strand cDNA probe used in the RAP screening was synthesized from 0.5 μg poly(A)+ mRNA in the presence of 1.5 μM [γ-[$^{32}$P] dCTP (3000 mCi/mmol) using an oligo(dT)$_{15}$ primer (Promega) and 15U MMLV reverse transcriptase according to the manufacturer's instructions (Promega). The labeled first-strand cDNA was separated from unincorporated radioisotope by G-50 column purification (ProbeQuant G-50 Micro Column, Pharmacia, New Jersey). Blots were prehybridized for 30 min in 1 mM EDTA, 0.25 M phosphate buffer (pH 7.2), 7% (w/v) SDS, and hybridized overnight at 60° C. in the same solution containing the denatured probe. Hybridized filters were washed twice for 30 min each at 60° C. in Wash Solution One (1 mM EDTA, 40 mM phosphate buffer, pH 7.2, 5% (w/v) SDS) and three times for 30 min each at 65° C. in Wash Solution Two (1 mM EDTA, 40 mM phosphate buffer pH 7.2, 1% (w/v) SDS). The air-dried filters were subjected to autoradiography to visualize hybridizing fragments.

In one reaction (template diluted to $10^{-7}$), a 600 bp fragment was detected that showed a very strong signal intensity after hybridization, indicating that it represented an abundant transcript in post harvest apple fruit. The fragment was isolated, cloned, and sequenced. The abundant product exhibited nucleotide sequence homology to plant genes encoding thiamine biosynthetic enzymes (Thi).

The tissue distribution of Fuji apple Thi transcript was determined by Northern blot analysis. The Thi cDNA fragments were hybridized to RNA from fruit (post harvest), ovary, root, and leaf tissue on Northern blots. The 1500 nucleotide Fuji Thi transcript was found to be abundant in fruit, and detectable in leaf tissue, but almost undetectable in root and ovary, indicating that Fuji Thi is highly fruit-specific. The Fuji Thi cDNA fragment was also used as a probe on Fuji and Gala genomic Southern blots to determine gene copy number. The results indicate that there are two similar copies of Thi in both the Fuji and Gala apple genomes.

Isolation Of An Apple Fruit-Associated Thi-1 Promoter

An oligonucleotide primer was designed based on the sequence of the Thi-RAP cDNA fragment, and used to walk upstream in the Fuji genome and eventually isolate an upstream regulatory region that functions as a post-harvest fruit-specific promoter. The oligonucleotide primer Thi 3' R (SEQ ID NO:7), was used in the amplification of upstream sequences from a PCR-accessible Fuji apple genomic library. A number of genomic DNA fragments were amplified using Thi 3' R (SEQ ID NO:7) and Thi700R (SEQ ID NO:8) primers, cloned, and sequence analysis performed. The results indicated that 2 copies of the Fuji Thi gene were represented in the isolated products. The two Fuji Thi genes differ in the size and sequence of an intron that interrupts the coding region; in Thi-1, the intron is 747 bp, while in Thi-2, 301 bp.

From the analysis of genomic fragments, a forward primer, Thi 4BF (SEQ ID NO:9), was designed which would amplify both Thi genes from the Fuji genome. Several nucleotide differences between Thi-1 and Thi-2 were evident in the coding region, including an approximately 4% difference at the nucleotide level, and the presence of a diagnostic restriction site (SmaI) in Thi -I, that is absent in Thi-2. Taking advantage of these differences in nucleotide sequence between Thi-1 and Thi-2, it was determined that the Thi transcript present in Fuji apple fruit is encoded by Thi-1.

It was determined that Thi-1 encodes a fruit-associated transcript, and Thi-1 sequence-specific primers were designed that preferentially amplify upstream sequences associated with the fruit-associated gene. These primers were used to walk upstream in a PCR-accessible Fuji apple genomic library (Universal Genome Walker Kit, Clontech Laboratories, Inc., Palo Alto, Calif.). The libraries were constructed and amplified according to the supplier's protocol. In addition to the five restriction endonucleases included in the kit, four other blunt-cutters were used to digest genomic DNA prior to adaptor ligation: BbrPI, HpaI, MscI, and SnaBI. A 1.2 kb product was amplified from the DraI library after two rounds of amplification of the Fuji genomic libraries using ThiG5' Rev1 (SEQ ID NO:10) and AP1 (SEQ ID NO:27) in the primary reaction and ThiG5' Rev2 (SEQ ID NO: 11) and AP2 (SEQ ID NO:28) in the secondary reaction. Primers were designed based on the sequence of the 1.2 kb product for another upstream walk. A 1 kb product was amplified from the HpaI library after two rounds of amplification of the Fuji apple genomic libraries using ThiG5' Rev5 (SEQ ID NO: 12) and AP1 (SEQ ID NO:27) in the primary reaction and ThiG5' Rev6 (SEQ ID NO: 13) and AP2 (SEQ ID NO:28) in the secondary reaction. The 1.2 kb and 1 kb Genome Walker products were assembled as a contiguous sequence, and the assembled sequence used to design primers for amplification of the complete Thi-1 upstream promoter sequence directly from Fuji genomic DNA.

A HindIII restriction site was engineered into the 5' primer, ThiG5' (SEQ ID NO: 14) and an NcoI site was engineered around the start codon in the 3' primer ThiGNco3' (SEQ ID NO: 15), for ease of cloning.

When ThiG5' (SEQ ID NO: 14) and ThiGNco3' (SEQ ID NO: 15) were used to amplify the Thi-1 upstream regulatory region from Fuji genomic DNA, 1.3kb (SEQ ID NO: 1) and 975 bp (SEQ ID NO:2) amplification products were obtained. Analysis of these amplification products revealed that the 5' end of the 1.3kb fragment had nucleotide sequence homology to 5S ribosomal RNA genes, while the 975 bp fragment does not. Otherwise, the two sequences were essentially identical. Both upstream sequences contain putative TATA boxes and have a high A/T percentage.

The amplified Thi-1 promoters were digested to produce the appropriate cohesive ends and cloned into compatible sites in a reporter gene construct, comprised of the promoter translationally fused with GUS and containing the nos3' terminator, with the resulting constructs designated, pAG162 and pAG 162a, respectively. The nucleotide sequence of the Thi-1 promoters, as they exist in pAG162 and pAG162a, are presented in FIGS. 1 and 2, respectively.

A Basic BLASTN search of non-redundant nucleic acid sequence databases through NCBI, which can be carried out using the search capabilities of the NIH website, revealed no significant matches to the 1.3 kb and 975 bp Thi-1 promoters, as presented in (SEQ ID NO:1, FIG. 1) and (SEQ ID NO:2, FIG. 2), respectively.

EXAMPLE 2

Construction of an Apple Thi-1:Melon Actin Fusion Promoter

The Fuji Thi 1.3 promoter was fused to a melon actin promoter at the TATA-box. Both promoters contain a canonical plant TATA-box (TATAAA), facilitating a perfect fusion between them at that site. Chimeric oligonucleotide primers were designed that were complementary to both of the promoter sequences.

A fragment containing the Fuji Thi promoter from the 5' end to the TATA box was amplified from pAG162 using 1233 (SEQ ID NO: 19) and (Act)Thi_R (SEQ ID NO: 17). The melon actin fragment was amplified from pAG 167 using GUS5' R (SEQ ID NO: 18) and (Thi)Act_F (SEQ ID NO: 16). Both sets of amplifications were carried out using a PE480 thermal cycler under the following conditions: 25 cycles [94° C., 30sec.; 60° C., 30 sec.; 72°C.,90 sec.], 1 cycle [72° C., 10 min.]. The amplification of pAG167 yielded a 1.2 kb fragment from the melon actin promoter containing the transcription start site, a 5' UTR intron, and the translational start site that had been engineered to contain an NcoI site for ease of subcloning.

The Fuji Thi and melon actin fragments contained a complementary overlapping region of 20 nt. The two fragments were fused by combining them in a second amplification reaction and using the end primers, 1233 (SEQ ID NO:19) and GUS5' R (SEQ ID NO:18) for amplification using a PE480 thermal cycler under the following conditions: 25 cycles [94° C., 30 sec; 60° C., 30 sec; 72° C., 150 sec], 1 cycle [72° C., 10 min]. The resulting reaction products were separated on an agarose gel, and a fragment of the correct predicted size was gel purified, digested with HinDIII and NcoI, then ligated into a vector containing the reporter gene GUS and given the designation pAG752. The complete sequence of the Fuji Thi 1.3:actin fusion (SEQ ID NO:3), as it exists in pAG752 is presented in FIG. 3. HinDIII and NcoI restriction sites were engineered into the 5' and 3' ends of the promoter fragment, respectively, to aid in subcloning.

EXAMPLE 3

Isolation Of An Apple Fruit-Associated MADS2 Promoter mRNA was isolated from developing Fuji apple ovaries as previously described, and a PCR-accessible cDNA library was constructed (Marathon cDNA Amplification Kit, Clontech, Palo Alto, Calif.). A rapid amplification of cDNA 5' ends (5' RACE) reaction was performed with adaptor-specific and a MADS2 gene-specific oligonucleotide primer, apMADSPFa2, (SEQ ID NO:20). The 5' end of the Fuji MADS2 cDNA was amplified using the manufacturer's suggested conditions for RACE amplifications. A 5' RACE product of 400 bp was isolated, cloned, and sequenced. The 5' RACE product showed homology to the known 5' UTR, MADSBOX and variable region of the MADS2 cDNA clone. A putative translational start site was identified and gene-specific oligonucleotides were designed to walk upstream in a Fuji apple genomic library.

MADS2-specific primers were designed from the nucleotide sequence of the 5' RACE product and used to walk upstream in a PCR-accessible Fuji apple genomic library (Universal Genome Walker Kit, Clontech, Palo Alto, Calif.). The libraries were constructed and screened according to the supplier's protocol. In addition to the five restriction endonucleases included in the kit, four other blunt-cutters were used to digest genomic DNA prior to adaptor ligation: BbrPI, HpaI, MscI, and SnaBI. A 750 bp product was amplified from the EcoRV library after two rounds of amplification of the Fuji apple genomic libraries using apMADSPFa3 (SEQ ID NO:21) and AP1 (SEQ ID NO:27) in the primary reaction and apMADSPFb2 (SEQ ID NO:23) and AP2 (SEQ ID NO:28) in the secondary reaction. Primers were designed from the nucleotide sequence of the 750 bp amplification product for use in another upstream walk. A 720 bp product was amplified from the HpaI library after two rounds of amplification of the Fuji apple genomic libraries using apMADSPFa4 (SEQ ID NO:22) and AP1 (SEQ ID NO:27) in the primary reaction and apMADSPFb3 (SEQ ID NO:24) and AP2 (SEQ ID NO:28) in the secondary reaction.

The 400 bp RACE product, and the 750 bp and 720 bp GenomeWalker products were assembled as a contiguous sequence which was used to design primers to amplify the complete MADS2 upstream sequence directly from genomic DNA. An NcoI site was engineered around the start codon, for ease of cloning in-frame with a heterologous coding sequence. A complete MADS2 promoter was amplified from Fuji apple genomic DNA with the MADS2-5' (SEQ ID NO:25) and MADS2Nco (SEQ ID NO:26) primer pair.

The isolated MADS2 promoter was subcloned into a reporter gene construct which has the promoter translationally fused with GUS and contains the nos terminator sequence. The resulting MADS2 promoter::reporter gene construct was designated pAG 168.

The MADS2 promoter sequence exhibits a high A/T percentage, contains a putative TATA box and two "GAGA" boxes that are known to exist in the 5' UTR of the Fuji MADS2 cDNA. The nucleotide sequence of the MADS2 promoter, as it exists in pAG 168, is presented in FIG. 4 (SEQ ID NO:4). A Basic BLASTN search (http://www.ncbi.nlm.nih.gov/BLAST) of non-redundant nucleic acid sequence databases through NCBI (http://www.ncbi.nlm.nih. gov/index.html) with the MADS2 promoter sequence revealed sequence identity between the 5'UTR of the MADS2 cDNA (*Malus domestica* sequence, GenBank accession number U78948; Sung, Yu and An, unpublished), and nucleotides 865 to 971 of the MADS2 promoter, as presented in SEQ ID NO:4.

EXAMPLE 4

Construction Of Plant Transformation Vectors And Evaluation Of Promoter Activity Using Reporter Constructs The relative activity of the apple fruit-associated and Thi 1.3:actin fusion promoters was determined using a transient assay system employing the GUS reporter gene. The transient assay is based on particle bombardment of plant tissue sections with a suspension of DNA and gold particles, as described below.

Specific equipment and reagents employed in particle bombardment include the BioRad Biolistic PDS-1000/He system (BioRad Laboratories, Hercules, Calif., USA), gold particles of 1.5–3.0 μm (Aldrich, Milwaukee, Wis., USA), a rupture disk: 1,100 PSI (BioRad Laboratories, Hercules, Calif., USA), stop screens of 0.685 mesh (Rumsey-Loomis, Freeville, N.Y.), macrocarriers: (Rumsey-Loomis, Freeville, N.Y.) and X-Gluc: 5-Bromo-4-chloro-3-indoyl β-D-glucuronide cyclohexylamine salt (Rose Scientific, Edmonton, Alberta, Canada).

Solutions for use in GUS assays included: 50% Glycerol (vol/vol); 2.5M calcium chloride ($CaCl_2$, 13.875 grams anhydrous $CaCl_2$ dissolved in 50 mls sterile $diH_2O$); 0.1M spermidine (0.1452 grams dissolved in 10 mls sterile $diH_2O$); 70% EtOH (vol/vol), 3 mls sterile $diH_2O$ in 7 mls 200 proof ethyl alcohol; X-gluc solution (200 ml prepared by adding the components in the amounts shown in Table 1, below, to 198 ml distilled $H_2O$, stirring for 10 minutes or until dissolved, adjusting the pH to 7.0, dissolving 100 mg X-gluc in 2 ml DMSO, adding X-gluc/DMSO solution to the pH 7.0 solution, rinsing the X-gluc vial twice using the pH 7.0 solution, and filter sterilizing the resultant solution).

TABLE 1

Solutions for GUS Assay.

| Component | Amount | Final Conc. |
| --- | --- | --- |
| EDTA, Disodium salt | 0.744 g | 10.0 mM |
| $NaH_2PO_4.H_2O$ monobasic, monohydrate | 1.760 g | 100.0 mM |
| $K_4Fe(CN)_6.3 H_2O$ | 0.042 g | 0.5 mM |
| Triton X-100 | 0.200 ml | 0.1% |

Gold particle suspensions were prepared by adding 30 μl of gold particles (1.5 μm to 3.0 μm) to a high quality microcentrifuge tube followed by addition of 1 ml 70% EtOH. The suspension was vortexed for 20 seconds and left to stand for 25 minutes, allowing the particles to settle to the bottom of the tube so that they do not stick to the side of the tube when centrifuging, followed by centrifuging in a microcentrifuge for 6 minutes at 13,000 rpm. The supernatant was carefully removed, discarded and 500 μl sterile $diH_2O$ added to the tube which was vortexed for 10 seconds and left standing for 25 additional minutes, followed by centrifuging in a microcentrifuge for 6 minutes at 13,000 rpm. The supernatant was again carefully removed, discarded, 500 μl sterile 50% glycerol stock added and the mixture vortexed until the particles were resuspended.

DNA solutions containing the GUS recombinant nucleic acid constructs were prepared by adding 50 μl (1 μg/μl) DNA to a microcentrifuge tube containing the gold and gently vortexing for 2–3 seconds, followed by the addition of 500 μl cold $CaCl_2$ (2.5M) and gentle vortexing for 2–3 seconds. This was followed by the addition of 200 μl cold spermidine (0.1M), gently vortexing at low speed (4° C.), tapping the tube a couple of times every 5–10 minutes to make sure particles remained suspended for a total vortex time of about 40 minutes. Centrifuge tubes were then pulsed to a maximum of 1,500 rpm in a microcentrifuge at 4° C., three times, with the supernatant removed and discarded. 1 ml cold 70% ethanol was then added, the solution mixed and the pulse centrifuge step repeated with the supernatant removed and discarded. This pulse centrifuge step was repeated using cold 100% EtOH, followed by the addition of 350 μl cold 100% EtOH and resuspension of the particles by gentle vortexing for 2 seconds.

Fruit was prepared for particle bombardment by wiping with a towel soaked in 95% ethyl alcohol, trimming off stem and bud ends and placing in a beaker. An amount of a water/soap mix (4 drops antimicrobial soap/1000 ml $H_2O$) sufficient to cover the fruit was added and shaken intermittently for 15 minutes, then rinsed with $diH_2O$, until the soap was gone. An amount of 75% EtOH sufficient to cover the fruit was then added and shaken gently each minute for 4 minutes, the EtOH drained off and an amount of 10% bleach/2 drops Tween 20/1000 ml sufficient to cover the fruit was added and the beaker shaken intermittently for 10 minutes. The bleach was drained off and the fruit rinsed 3 times with sterile $diH_2O$, followed by rinsing once with sterile 500 ml $diH_2O$/2 ml PPM mix (Plant Preservative Mixture, Plant Cell Technology, Washington, D.C.), and soaking in media consisting of filter sterilized 200 mg/l ascorbic acid and 200 mg/l citric acid, until ready to be cut. Before cutting, the fruit is blotted dry on filter paper.

Tissues for use in GUS assays include sterilized immature and mature fruit of apple, peach, and pear, at all stages of ripening from the immature ovary stage to fully mature, ripe fruit.

After cutting, the fruit was plated onto PAC 1 medium containing: MS salts, B5 vitamins, glycine 2 mg/l, sucrose 3%, casein hydrolysate 100 mg/l, BA 0.5 mg/l, 2,4-D 1.5 mg/l, PPM 5 ml/l, ascorbic acid 100 mg/l, citric acid 100 mg/l, cefotaxime 200 mg/l (aa) pH 5.8, phytagel 0.25.

The fruit tissue was bombarded using GUS reporter constructs, then sealed with parafilm and left in the dark at 24° C. for 22 hours. Explants were carefully transferred to clean, sterile petri plates and X-gluc solution added to completely cover the fruit. Plates were stored in an incubator at 37° C. for 18 hours, the X-gluc solution drained off and 95% EtOH added to cover the fruit. Observations were made using a microscope and counting the number of GUS foci on each slice of fruit.

The relative activities of a Thi 1.3, Thi 1.0, Thi 1.3:actin, MADS2 and the positive control constitutive promoter, CsVMV, were evaluated in transient assays for GUS expression in developing apple and pear fruit and in apple and pear leaves. Tables 2 through 6 present the results of transient GUS expression assays in slices of immature apple fruit (2.5 cm diameter, 5–6 seeds), developing fruit (4.5 cm diameter, 3–6 seeds) and mature fruit (5.5 cm diameter, 3–6 seeds) relative to assay results from apple leaves.

The activity of the apple promoters [(as measured by mean number of GUS foci or percent of fruit slices with foci (plus or minus the standard deviation, "SD")] was shown to increase during fruit development, peak in mature fruit and the relative promoter activity in mature fruit was shown to be greater than the activity in leaves.

Tables 7 through 11 show the results of transient assays where GUS expression is under the control of a Thi 1.3, Thi 1.0, Thi 1.3:actin, MADS2 or CsVMV promoter, respectively, in immature pear fruit (2.5 cm diameter, 9–10 seeds), developing pear fruit (3.5 cm diameter, 9–10 seeds) and mature pear fruit (5 cm diameter, 9–10 seeds).

The results were compared to the results of GUS expression assays in leaves using the same promoters. Similar to the results obtained in apple, the relative activity of the apple fruit associated promoters was greater in more mature pear fruit, at which time the activity in fruit was much greater than in the leaves. These data support the conclusion that the Thi 1.3, Thi 1.0, Thi 1.3:actin and MADS2 promoters are effective to promote gene expression in mature fruit of other species, and confirm that the activity of the promoters is fruit-associated.

TABLE 2

Transient GUS Assay in Developing Apple Fruit and in Leaves

| Promoter | Total # of fruit slices or leaves bombarded | Number of slices with GUS foci (%) | Mean # of foci/slice (SD) |
| --- | --- | --- | --- |
| Fuji Thi 1.3 (immature fruit) | 30 | 5 (17) | 2.6 (2.5) |
| Fuji Thi 1.3 (developing fruit) | 32 | 2 (6) | 4 (2.8) |
| Fuji Thi 1.3 (mature fruit) | 32 | 11 (34) | 3.3 (4.3) |
| Fuji Thi 1.3 (leaves) | 24 | 4 (17) | 4.3 (3.3) |

TABLE 3

Transient GUS Assay in Developing Apple Fruit and in Leaves.

| Promoter | Total # of fruit slices or leaves bombarded | Number of slices with GUS foci (%) | Mean # of foci/slice (SD) |
| --- | --- | --- | --- |
| Fuji Thi 1.0 (immature fruit) | 30 | 1 (3) | 2 (0) |
| Fuji Thi 1.0 (developing fruit) | 32 | 2 (6) | 4 (4.2) |
| Fuji Thi 1.0 (mature fruit) | 32 | 7 (22) | 1.4 (0.8) |
| Fuji Thi 1.0 (leaves) | 24 | 4 (17) | 3 (1.2) |

TABLE 4

Transient GUS Assay in Developing Apple Fruit and in Leaves.

| Promoter | Total # of fruit slices or leaves bombarded | Number of slices with GUS foci (%) | Mean # of foci/slice (SD) |
| --- | --- | --- | --- |
| Fuji Thi -actin (immature fruit) | 30 | 3 (10) | 5.3 (5.9) |
| Fuji Thi -actin (developing fruit) | 32 | 4 (13) | 1.3 (0.5) |
| Fuji Thi -actin (mature fruit) | 32 | 9 (28) | 1.9 (0.9) |
| Fuji Thi -actin (leaves) | 24 | 4 (17) | 1 (1) |

TABLE 5

Transient GUS Assay in Developing Apple Fruit and in Leaves.

| Promoter | Total # of fruit slices or leaves bombarded | Number of slices with GUS foci (%) | Mean # of foci/slice (SD) |
| --- | --- | --- | --- |
| Fuji MADS2 (immature fruit) | 30 | 0 | 0 |
| Fuji MADS2 (developing fruit) | 32 | 1 (3) | 1 (0) |
| Fuji MADS2 (mature fruit) | 32 | 2 (6) | 1 (0) |
| Fuji MADS2 (leaves) | 24 | 2 (8) | 1 (1) |

TABLE 6

Transient GUS Assay in Developing Apple Fruit and in Leaves.

| Promoter | Total # of fruit slices or leaves bombarded | Number of slices with GUS foci (%) | Mean # of foci/slice (SD) |
| --- | --- | --- | --- |
| CsVMV (immature fruit) | 30 | 10 (33) | 3 (2.8) |
| CsVMV (developing fruit) | 32 | 8 (25) | 2.4 (1.7) |
| CsVMV (mature fruit) | 32 | 7 (22) | 3.1 (3.1) |

TABLE 6-continued

Transient GUS Assay in Developing Apple Fruit and in Leaves.

| Promoter | Total # of fruit slices or leaves bombarded | Number of slices with GUS foci (%) | Mean # of foci/slice (SD) |
|---|---|---|---|
| CsVMV (leaves) | 24 | 10 (42) | 2.9 (1.6) |

The Fuji Thi 1.3, Thi 1.0 and Thi 1.3:actin promoters were particularly active in mature 5 apple fruit. A comparison to the activity of the constitutive promoter CsVMV (Table 6) and the MADS2 promoter (Table 5) to the activity of the Fuji Thi 1.3 promoter (Table 2), the Thi 1.0 promoter (Table 3), and the Thi 1.3:actin promoter (Table 4) indicates that the Fuji Thi 1.3, Thi 1.0 and Thi 1.3:actin promoters have greater relative activity in mature apple fruit and lower relative activity in leaves.

In contrast, in developing and mature pear fruit, the Thi 1.3, Thi 1.0, and MADS2 apple promoters showed similar activity in the transient assay. All three promoters were active in developing and mature pear fruit and were significantly less active in leaves, as shown for the Thi 1.3 promoter (Table 7), the Thi 1.0 promoter (Table 8), the Fuji Thi 1.3:melon actin fusion promoter (Table 9), and the MADS2 promoter (Table 10).

TABLE 7

Transient GUS Assay in Developing Pear Fruit and in Leaves.

| Promoter | Total # of fruit slices or leaves bombarded | Number of slices with GUS foci (%) | Mean # of foci/slice (SD) |
|---|---|---|---|
| Fuji Thi 1.3 (immature fruit) | 30 | 0 | 0 |
| Fuji Thi 1.3 (developing fruit) | 32 | 8 (25) | 1 (1) |
| Fuji Thi 1.3 (mature fruit) | 32 | 12 (38) | 2.2 (1.3) |
| Fuji Thi 1.3 (leaves) | 27 | 6 (22) | 1.3 (0.8) |

TABLE 8

Transient GUS Assay in Developing Pear Fruit and in Leaves.

| Promoter | Total # of fruit slices or leaves bombarded | Number of slices with GUS foci (%) | Mean # of foci/slice (SD) |
|---|---|---|---|
| Fuji Thi 1.0 (immature fruit) | 30 | 1 (3) | 1 (1) |
| Fuji Thi 1.0 (developing fruit) | 32 | 11 (34) | 1.3 (0.6) |
| Fuji Thi 1.0 (mature fruit) | 32 | 10 (31) | 2.1 (1.4) |
| Fuji Thi 1.0 (leaves) | 27 | 0 | 0 |

TABLE 9

Transient GUS Assay in Developing Pear Fruit and in Leaves.

| Promoter | Total # of fruit slices or leaves bombarded | Number of slices with GUS foci (%) | Mean # of foci/slice (SD) |
|---|---|---|---|
| Fuji Thi -actin (immature fruit) | 30 | 1 (3) | 2 (2) |
| Fuji Thi -actin (developing fruit) | 32 | 16 (50) | 2.6 (1.6) |
| Fuji Thi -actin (mature fruit) | 32 | 19 (59) | 4 (3.5) |
| Fuji Thi -actin (leaves) | 27 | 3 (11) | 5 (2.6) |

TABLE 10

Transient GUS Assay in Developing Pear Fruit and in Leaves.

| Promoter | Total # of fruit slices or leaves bombarded | Number of slices with GUS foci (%) | Mean # of foci/slice (SD) |
|---|---|---|---|
| Fuji MADS2 (immature fruit) | 30 | 0 | 0 |
| Fuji MADS2 (developing fruit) | 32 | 6 (19) | 1.3 (0.8) |
| Fuji MADS2 (mature fruit) | 32 | 13 (41) | 3.7 (2.9) |
| Fuji MADS2 (leaves) | 27 | 5 (19) | 2 (1.4) |

TABLE 11

Transient GUS Assay in Developing Pear Fruit and in Leaves.

| Promoter | Total # of fruit slices or leaves bombarded | Number of slices with GUS foci (%) | Mean # of foci/slice (SD) |
|---|---|---|---|
| CsVMV (immature fruit) | 30 | 6 (20) | 2.3 (2.4) |
| CsVMV (developing fruit) | 32 | 11 (34) | 2.2 (1.5) |
| CsVMV (mature fruit) | 32 | 28 (88) | 3.6 (2.8) |
| CsVMV (leaves) | 27 | 14 (52) | 4.6 (6.9) |

The reasults of tansient assays for GUS expression in pear fruit and leaves showed that the Fuji Thi 1.0 and MADS2 promoters were particularly active in developing and mature pear fruit, with much greater activity in fruit relative to leaves. The MADS2 and CsVMV promoters were also most active in mature fruit. In addition, activity was also evident in developing fruit and leaves for MADS2 and in all tissues for CsVMV.

Although the Fuji Thi 1.3:melon actin fusion promoter demonstrated similar relative activity to that of the Thi 1.3 promoter in apple fruit (Table 4 vs. Table 2), the Fuji Thi 1.3:melon actin fusion promoter demonstrated greater relative activity in developing and mature pear fruit (Table 9 Vs. Table 7), indicating that the Thi 1.3:actin fusion promoter find utility in the control of gene expression in heterologous species.

TABLE 12

Sequences Provided In Support Of The Invention.

| Description | SEQ ID NO. |
|---|---|
| FIG. 1: The complete nucleotide sequence of Thi-I(1.3 kb) promoter. (nucleotides 1-321) | 1 |
| FIG. 2: The complete nucleotide sequence of Thi-1(975 bp) promoter. (nucleotides 1-985) | 2 |
| FIG. 3: The complete nucleotide sequence of the Fuji Thi 1.3-Actin fusion as in pAG-752. | 3 |
| FIG. 4: The complete nucleotide sequence of MADS2 promoter. (nucleotides 1-1038) | 4 |
| MAR AP1 5' CCATCCTAATACGACTCACTATA-GGGC 3' | 5 |
| CSP 5' GGGCAGGTTTCTAGAATTCAGCGGCCGC 3' | 6 |
| Thi 3'R 5'-CTCGGCAACTTCCATGCCGGTGACG-3' | 7 |
| Thi700R 5'-CGAGCTCGTTAAGGAAGAGATGGGC-3' | 8 |
| Thi 4BF 5'-TCAGGTCGCCATCATAGAGCAGTCCG-3' | 9 |
| ThiG5'Rev1 5'-AAGCACCCGGAAACTCTTAAACGACCAAAA-3' | 10 |
| ThiG5'Rev2 5'-AAATGACAGTAATTACCATGGCAGAGA-3' | 11 |
| ThiG5'Rev5 5'-GTCTTACTTTGAAACAGTCTCCTTAG-3' | 12 |
| ThiG5'Rev6 5'-ACTACGCTCCACATAAGCAAAGTCAT-3' | 13 |
| THIG5' 5'-ATTTAAGCTTTAGATCTCATGGGCGATGTGGGGATGT-3' | 14 |
| THIGNco3' 5'- GCCTTGGTTGCCATGGATTGATGCGAG-3' | 15 |
| (Thi)Act_F: 5'CAATTCCCTTATAAACCCCCGTTTC | 16 |
| (Act)Th_R: 5'GGGGGTTTATAAGGGAATTGCTAAG | 17 |
| GUS5'R: GACTTCGCGCTGATACC | 18 |
| 1233: AGCGGATAACAATTTCACACAGGA | 19 |
| apMADSPFa2 5'-GCTGCCTCTCTGTATATGAGTATCTTTC-3' | 20 |
| apMADSPFa3 5'-ATACGGTTGTTCCTGCTGAACTGATCTCT-3' | 21 |
| apMADSPFa4 5'-TTCCCGGGCCCGTATGGCTCGAAACCACA-3' | 22 |
| apMADSPFb2 5'-GAAACCAGAAATCCCACCAAGAAACCAAT-3' | 23 |
| apMADSPFb3 5'-AGGGTATAGTGCTATTTCCACGTTCATTC-3' | 24 |
| MADS2-5' 5'-CGCCGTCGCTGAACTCGATCC-3' | 25 |
| MADS2Nco 5'-CTCCCCATGGTCTCTCTAACA-3' | 26 |
| GenomeWalker AP1 primer: 5'-GTAATACGACTCACTATAGQGC-3' | 27 |
| GenomeWalker API primer: 5'-ACTATAGGGCACGCGTGGT-3' | 28 |

It is claimed:

1. An isolated nucleic acid sequence comprising an apple promoter selected from the group consisting of a Thi-1 promoter having the nucleotide sequence presented as SEQ ID NO:1 or SEQ ID NO:2, a MADS2 promoter having the nucleotide sequence presented as SEQ ID NO:4, and a Fuji Thi 1.3-Actin fusion promoter having the nucleotide sequence presented as SEQ ID NO:3.

2. The isolated nucleic acid sequence of claim 1, wherein said apple promoter or a functional portion thereof demonstrates greater activity in fruit relative to roots, ovaries and/or leaves and has a sequence selected from the group consisting of a Thi-1 promoter having the sequence presented as SEQ ID NO:1 or SEQ ID NO:2 and a Fuji Thi 1.3-Actin fusion promoter having the sequence presented as SEQ ID NO:3.

3. A plant expression vector comprising the isolated nucleic acid sequence of claim 1 or 2.

4. The plant expression vector of claim 3, further comprising a heterologous nucleic acid coding sequence operably linked to said promoter.

5. The plant expression vector of claim 4, further comprising a selectable marker-encoding nucleic acid sequence operably linked to a promoter.

6. The plant expression vector of claim 4, further comprising control sequences recognized by a host cell transformed with the vector, said control sequences operably linked to the heterologous nucleic acid coding sequence and said promoter.

7. A plant cell comprising the plant expression vector of claim 6.

8. A mature plant comprising the plant cell of claim 7.

9. A method of expressing a heterologous nucleic acid sequence in a plant cell, by carrying out the steps of:
   (a) introducing a nucleic acid construct comprising the plant expression vector of claim 6A under conditions effective to stably incorporate said encoding nucleic acid sequences into the plant cell;
   (b) culturing said plant cell in a culturing medium containing a selection agent;
   (c) selecting for transformed plant cells, wherein said heterologous nucleic acid coding sequence is expressed.

10. A method for producing a transgenic plant, comprising;
   (a) introducing a heterologous nucleic acid construct comprising the plant expression vector of claim 4A under conditions effective to stably incorporate said nucleic acid coding sequences into the plant cells to yield transformed progenitor cells;
   (b) selecting for transformed progenitor cells in culturing medium containing a selection agent;
   (d) regenerating said selected progenitor cells to produce a transgenic plant.

11. The plant expression vector of claim 4, wherein said heterologous nucleic acid coding sequence encodes S-adenosyl methionine hydrolase (SAMase).

12. A plant cell comprising an isolated nucleic acid sequence of claim 1.

13. An isolated promoter, which in native plants is located upstream of and controls the expression of a gene encoding an enzyme involved in thiamine biosynthesis, wherein said promoter has the sequence presented as SEQ ID NO:1 or SEQ ID NO:2.

14. An isolated plant promoter, which in native plants is located upstream of and controls the expression of a MADS2 gene encoding a polypeptide identified as an ovary-specific transcript in apple, wherein said promoter has the sequence presented as SEQ ID NO:4.

15. The method of claim 9, wherein the expression of said nucleotide coding sequence is fruit-preferred.

* * * * *

SEQUENCE LISTING

<160> NUMBER OF SEQ ID NOS: 28

<210> SEQ ID NO 1
<211> LENGTH: 1321
<212> TYPE: DNA
<213> ORGANISM: Artificial Sequence
<220> FEATURE:
<223> OTHER INFORMATION: promoter

<400> SEQUENCE: 1

```
aagctttaga tctcatgggc gatgtgggat gtcacaatcc accccccctta ggggcccgac    60 gtcctcgtca tcacacttcc ggccagggat tggctctaat accatttgtc acatcccggc   120
ccggatccac cacatctcaa gcccgttcca ccaccgtagc atgatattgt ccgctttggg   180
cttaccattc cctcacggtt ttgttttttgg gaactcacga gcaacttcct agtgggtcac   240
ccatcctggg agtgttttaac ttcggagttc ctacgaaacc cgaagccaat gagctcccaa   300
aaggtctcgt gctaagtagg gatgagaata tacatttaag gattactccc ctgggcgatg   360
tgggatgtca caatttgggt aagaaaatga caagatcaaa ttaaaactgt caaatttttat   420 gcaaatttga aaaacaatta caaatctta aggaaagtat aacattagtg cttttttttt   480
tgttccaaga agcattaaca tacaatttgt tatgatatat taatatgcaa tgatttaaa   540 cattaatgca tttttttttc attaatccct cccttcaaat atgcatagaa tttaatgtat   600
```

| | |
|---|---|
| acattaaaac tttaattagg ggtgttttag gcatctaaaa aaatgcaaaa tgtgtaaagg | 660 |
| caaatagaat taatgacttt gcttatgtgg agcctagtca ttaggttttta tttagataaa | 720 |
| aagactatgt caggttttat gtaaagaaac ttgagtttca agagctaaag tcatattttc | 780 |
| agtagaaatt aaacacatta atcaacactt gagtaataaa atgatcatca acaatctaat | 840 |
| catttggttt acaaattgag aaatactaag gagactgttt caaagtaaga cttcctatga | 900 |
| actctctatc acctcatatt cttggcacaa aattttataa cattaacata agaattgtat | 960 |
| caacaacata aaatggcaga aagttcgtag aaaatcacat tcaagataat agccttagca | 1020 |
| attcccttat aaactttgtc atctaacatt tccctctcta ttcactctcc tcacactcaa | 1080 |
| acacacaccg tggactggtt catgcttgcc acttgtacct cccaagaggt tctagaccct | 1140 |
| tcatatccta tcctcttccc acgtgtccat cttcaatttt acatatacgt caccctcctc | 1200 |
| cttaaataac cactctcttc acttccatct tctgacttgc aaacgctaaa cccccaaatc | 1260 |
| accccatctt atcatcttct ctctctctcc ctctctctcc ttctctcgca tcaatccatg | 1320 |
| g | 1321 |

```
<210> SEQ ID NO 2
<211> LENGTH: 985
<212> TYPE: DNA
<213> ORGANISM: Artificial Sequence
<220> FEATURE:
<223> OTHER INFORMATION: promoter

<400> SEQUENCE: 2
```

| | |
|---|---|
| aagctttaga tctcatgggc gatgtgggga tgtcacaatt tgggtaagat aatgacaaga | 60 |
| tcaaattaaa actgtcaaat tttaggcaaa tttgaaaaac aattacaaaa tcttaaggaa | 120 |
| agtataacat tagtgctttt tttttgttcc aagaagcatt aacatacaat ttgttatgat | 180 |
| atattaatat gcagtgattt taaacattaa tgcattttt tttcattaac ccctcccttc | 240 |
| aaatatgcat agaatttaat gtatacatta aactttaat taggggtgtt ttaggcatct | 300 |
| aaaaaaatgc aaaatgtgta aaggcaaata gaattaatga ctttgcttat gtggagcgta | 360 |
| gtcattaggt tttatttaga taaaagact atgtcgggtt ttatgtaaag aaacttgagt | 420 |
| ttcaagagct aaagtcatat tttcagtaga aattaaacac attaatcaac acttgagtaa | 480 |
| taaaatgatc atcaacaatc taatcatttg gtttacaaat tgagaaatac taaggagact | 540 |
| gtttcaaagt aagacttcct atgaactctc tatcacctca tattcttggc acaaaatttt | 600 |
| ataacattaa cataagaatt gtatcaaaaa cataaaatga cagaaaattc gtagaaaatc | 660 |
| acattcaaga taatagcctt agcaattccc ttataaactt tgtcatctaa catttccctc | 720 |
| tctattcact ctcctcacac tcaaacacac accgtggact ggttcatgct tgccacttgt | 780 |
| acctcccaag aggttctaga cccttcatat cctatcctct tcccacgtgt ccatcttcaa | 840 |
| ttttacatat acgtcaccct cctccttaaa taaccactct cttcacttcc atcttctgac | 900 |
| ttgcaaacgc taaaccccca aatcacccca tcttatcatc ttctctctct ctccctctct | 960 |
| ctccttctct cgcatcaatc catgg | 985 |

```
<210> SEQ ID NO 3
<211> LENGTH: 2060
<212> TYPE: DNA
<213> ORGANISM: Artificial Sequence
<220> FEATURE:
<223> OTHER INFORMATION: promoter

<400> SEQUENCE: 3
```

```
aagctttaga tctcatgggc gatgtgggat gtcacaatcc acccccctta ggggcccgac      60
gtcctcgtca tcacacttcc ggccagggat tggctctaat accatttgtc acatcccggc     120
ccggatccac cacatctcaa gcccgttcca ccaccgtagc atgatattgt ccgctttggg     180
cttaccattc cctcacggtt ttgttttttgg gaactcacga gcaacttcct agtgggtcac     240
ccatcctggg agtgtttaac ttcggagttc ctacgaaacc cgaagccaat gagctcccaa     300
aaggtctcgt gctaagtagg gatgagaata tacatttaag gattactccc ctgggcgatg     360
tgggatgtca caatttgggt aagaaaatga caagatcaaa ttaaaactgt caagttttat     420
gcaaatttga aaacaatta caaaatctta aggaaagtat aacattagtg ctttttttttt     480
tgttccaaga agcattaaca tacaatttgt tatgatatat taatatgcaa tgattttaaa     540
cattaatgca tttttttttc attaatccct cccttcaaat atgcatagaa tttaatgtat     600
acattaaaac tttaattagg ggtgttttag gcatctaaaa aaatgcaaaa tgtgtaaagg     660
caaatagaat taatgacttt gcttatgtgg agcctagtca ttaggtttta tttagataaa     720
aagactatgt caggttttat gtaaagaaac ttgagtttca agagctaaag tcatattttc     780
agtagaaatt aaacacatta atcaacactt gagtaataaa atgatcatca acaatctaat     840
catttggttt acaaattgag aaatactaag gagactgttt caaagtaaga cttcctatga     900
actctctatc acctcatatt cttggcacaa aattttataa cattaacata agaattgtat     960
caacaacata aaatggcaga aagttcgtag aaaatcacat tcaagataat agccttagca    1020
attcccttat aaaccccgt ttctcttctt ccctcttcct cttattctcg tctttcaact    1080
cacctaggtc gacaacactc actcctctct cagccagacc ttcttctttg gagggttggc    1140
tctttcttct tcgttcgttc cttccttcct tcattcattc tcctctcttt catccaaggt    1200
ttgtttcttc cttcccttt ttaccaaatc ttctcacttc ccttacattt ttcatctggg    1260
gtatcgttct tttcccaaat tatgctgctt tcgtctctca tttatctact ttattgcttt    1320
taactcattt tcccttatgc ggttcttcaa ttttggctga tcttgctgtt tgttttggaa    1380
ttctgtttta atcgccctgg atccgaggtt tttgttcgta caatctacct agattctttc    1440
tgtttgtttg ctgatctgaa attttccatt tgggttttga ttgtctgtgc ttacggaact    1500
gagatctagg atttggagtt gtgtaccttt ttatttctgc atgcaattct gtaatcctgc    1560
atagctggat ggctttctgt tgattagtgc atgctttgtt taggacgaac tgacttggat    1620
ttttcgttgt cgatctgttc tatttttgt tttgctgttc tggttcatgc ttggaatgat    1680
ttagttgctt tgtaaattgt acactctgct tttgtgttag ttcacgtagc ttctcgatct    1740
gaaattggat atggttagag tttatggtca gcttgtgatc ttgcattatg caaaaattgg    1800
aactttaatc cttttcattt gtaagatctt taagatatct gattacctgg ttgatttttt    1860
tgtgtctgga ttattttatt tgttttgaaa gtagtttgtt ggttcttcct gtattatttg    1920
ctgaatcggg atgatcaatt atatgacgtg aatttatgga atgtaaatga atggtttaag    1980
agattgcttt gtgtggctta tttattcaat ttctattttt acatcgtttt gtgcaggttt    2040
tgaaaaaaaa gggcccatgg                                                2060
```

<210> SEQ ID NO 4
<211> LENGTH: 1038
<212> TYPE: DNA
<213> ORGANISM: Artificial Sequence
<220> FEATURE:
<223> OTHER INFORMATION: promoter

<400> SEQUENCE: 4

```
cgccgtcgct gaactcgatc cgtggcgcag tcgaatgcca gacccaactc aaaaccgagt        60
ttttccattt ttaattttt aagttttta ttatataaaa atattttttt aattatttac        120
atacttttag tttcacatgg taatgtttaa ttagatttgt gggacccatt tatgtgtcac       180
gtcagcccgt aacagaattt tttacgaaat tatcacattg atttgcgaca tctattttca       240
gagactacat tgattggttt ttaattttat aaaccatctt aatgaagtat gtcaatttta       300
aagatcattt attacaaaaa ccctttattt aattttatat tgaaatacta aaatatgata       360
aaatgtactc gaatagttta gtagataggg tggtgttatt tagatactta ttattttatt       420
tttatacata ctcttcttaa tttctaatca gaaaattgaa ttaataaaaa aatatcaatg       480
aaaaataatt taacaaaaat gtacaaaaat acagaatgaa cgtggaaata gcactatacc       540
ctagtagata ttggataaaa tatattatgg gtttaaaatt gaaaaaatat atgtggtttc       600
gagccatacg ggcccgggaa tgaccgactg ttgcagtgcc tctggccaat cccaactcga       660
caacgttttt gacgaaacca ctctggtttt ccaaccccac ccatttcact cttacagcgg       720
ttttgaaata tcctataaat atatcataca aatacaacag agaaattttt ttttttgtca       780
aaatatacaa cagagaattg agtcactcat atatagacag agaaggagag agaccagacc       840
cctaccttag agagagagag agagcagaag ccatctgtgt gtcaactggt tctttctctc       900
ccattttttct tggtttcttg gtgggatttc tggtttctct aaactaagag atcagttcag       960
caggaacaac cgtatatata ttactaggat tattaattat ttatttataa taataaataa      1020
ttgttagaga gaccatgg                                                    1038
```

<210> SEQ ID NO 5
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 5
ccatcctaat acgactcact atagggc        27

<210> SEQ ID NO 6
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 6
gggcaggttt ctagaattca gcggccgc        28

<210> SEQ ID NO 7
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 7
ctcggcaact tccatgccgg tgacg        25

<210> SEQ ID NO 8
<211> LENGTH: 25
<212> TYPE: DNA
<213> ORGANISM: Artificial Sequence

```
<220> FEATURE:
<223> OTHER INFORMATION: oligonucleotide primer

<400> SEQUENCE: 8
cgagctcgtt aaggaagaga tgggc                                    25

<210> SEQ ID NO 9
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 9
tcaggtcgcc atcatagagc agtccg                                   26

<210> SEQ ID NO 10
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 10
aagcacccgg aaactcttaa acgaccaaaa                               30

<210> SEQ ID NO 11
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 11
aaatgacagt aattaccatg gcagaga                                  27

<210> SEQ ID NO 12
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 12
gtcttacttt gaaacagtct ccttag                                   26

<210> SEQ ID NO 13
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 13
actacgctcc acataagcaa agtcat                                   26

<210> SEQ ID NO 14
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 14
atttaagctt tagatctcat gggcgatgtg gggatgt                       37
```

-continued

<210> SEQ ID NO 15
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 15
gccttggttg ccatggattg atgcgag                                    27

<210> SEQ ID NO 16
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 16
caattccctt ataaccccc gtttc                                       25

<210> SEQ ID NO 17
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 17
gggggtttat aagggaattg ctaag                                      25

<210> SEQ ID NO 18
<211> LENGTH: 17
<212> TYPE: DNA
<213> ORGANISM: Artificial Sequence
<220> FEATURE:
<223> OTHER INFORMATION: oligonucleotide primer

<400> SEQUENCE: 18
gacttcgcgc tgatacc                                               17

<210> SEQ ID NO 19
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 19
agcggataac aatttcacac agga                                       24

<210> SEQ ID NO 20
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 20
gctgcctctc tgtatatgag tatctttc                                   28

<210> SEQ ID NO 21
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 21
atacggttgt tcctgctgaa ctgatctct                29

<210> SEQ ID NO 22
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 22
ttcccgggcc cgtatggctc gaaaccaca                29

<210> SEQ ID NO 23
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 23
gaaaccagaa atcccaccaa gaaaccaat                29

<210> SEQ ID NO 24
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 24
agggtatagt gctatttcca cgttcattc                29

<210> SEQ ID NO 25
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 25
cgccgtcgct gaactcgatc c                21

<210> SEQ ID NO 26
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 26
ctccccatgg tctctctaac a                21

<210> SEQ ID NO 27
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 27
gtaatacgac tcactatagg gc                22

<210> SEQ ID NO 28

```
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 28
actatagggc acgcgtggt                                               19
```